United States Patent [19]

Draper

[11] 4,201,778

[45] May 6, 1980

[54] 6-ACYLOXY-1,4,6-PREGNATRIENES, THEIR USE AS ANTI-INFLAMMATORY AGENTS, METHODS FOR THEIR MANUFACTURE, AND 6-OXO-1,4-PREGNADIENE INTERMEDIATES

[75] Inventor: Richard W. Draper, North Caldwell, N.J.

[73] Assignee: Schering Corporation, Kenilworth, N.J.

[21] Appl. No.: 849,563

[22] Filed: Nov. 8, 1977

[51] Int. Cl.$^2$ .................... C07J 71/00; A61K 31/58
[52] U.S. Cl. .................... 424/241; 260/239.55 R; 260/239.55 D; 260/397.1; 260/397.45
[58] Field of Search .................... 260/239.55 D, 397.1, 260/397.45 D

[56] References Cited

U.S. PATENT DOCUMENTS

| | | | |
|---|---|---|---|
| 2,816,902 | 12/1957 | Gould et al. | 260/397.45 |
| 2,887,499 | 5/1959 | Carvajal | 260/397.45 |
| 2,937,975 | 5/1960 | Figdor | 167/65 |
| 3,032,565 | 5/1962 | Dodson et al. | 260/397.4 |
| 3,071,580 | 1/1963 | Holmlund et al. | 260/239.55 |
| 3,079,301 | 2/1963 | Gould et al. | 167/77 |
| 3,131,181 | 4/1964 | Dasza et al. | 260/239.55 |
| 3,629,303 | 12/1971 | Rausser et al. | 260/397.4 |
| 4,024,131 | 5/1978 | Villax | 260/397.45 |
| 4,076,708 | 2/1978 | Green et al. | 260/397.45 |

OTHER PUBLICATIONS

"Organic Reactions in Steroid Chemistry", vol. I, (1974), pp. 306–313.
L. L. Smith et al., J. Org. Chem., vol. 26 (1961), pp. 974–976.
J. P. Dusza et al., J. Org. Chem., vol. 28 (1963), pp. 760–763.
M. J. Green et al., J. Steroid Biochem., 6 (1975), pp. 599–605.
A. Bowers et al., J. Am. Chem. Soc. (1959), vol. 81, p. 5233.
Drug Research, vol. 5, pp. 35–39 (1963), E. Jucker.
R. Littell et al., J. Org. Chem. (1962), vol. 27, p. 2544.
Teutsch et al., J. Med. Chem. 16 (1973), pp. 1370–1376.
Hayano et al., Arch. Biochem. and Biophysics (1954), No. 2, p. 218.

*Primary Examiner*—Elbert L. Roberts
*Attorney, Agent, or Firm*—Mary S. King

[57] ABSTRACT

Novel 6-acyloxy-3,20-dioxo-1,4,6-pregnatrienes and 6-acyloxy-3,20-dioxo-4,6-pregnadienes, useful anti-inflammatory agents, are prepared by reaction of the corresponding 3,6,20-trioxo-1,4-pregnadiene or 3,6,20-trioxo-4-pregnene with an acyl halide or an acid anhydride in pyridine. Preferred anti-inflammatory agents are 6-alkanoyloxy-9α-halogeno-16-methyl-1,4,6-pregnatriene-3,20-diones. Also described are novel 6-oxo-9α-halogeno-16-substituted-1,4-pregnadienes, useful as intermediates in preparing the corresponding 6-acyloxy-1,4,6-pregnatrienes and which also exhibit anti-inflammatory activity per se.

30 Claims, No Drawings

6-ACYLOXY-1,4,6-PREGNATRIENES, THEIR USE AS ANTI-INFLAMMATORY AGENTS, METHODS FOR THEIR MANUFACTURE, AND 6-OXO-1,4-PREGNADIENE INTERMEDIATES

FIELD OF INVENTION

This invention relates to novel compositions-of-matter, methods for the manufacture thereof, pharmaceutical formulations thereof and methods of using said formulations in the treatment and control of inflammatory conditions.

More specifically, this invention relates to novel 6-acyloxy-3,20-dioxo-1,4,6-pregnatrienes and 6-acyloxy-3,20-dioxo-4,6-pregnadienes, pharmaceutical formulations thereof, and their use in the treatment and control of inflammatory conditions.

In particular, this invention relates to novel 6-acyloxy-9α-halogeno-1,4,6-pregnatriene-11β,17α,21-triol-3,20-dione 17-hydrocarboncarboxylates or 17,21-dihydrocarboncarboxylates, particularly the 16-methyl derivatives thereof, to pharmaceutical formulations thereof, and their use in the treatment and control of inflammation when applied topically.

This invention also includes the method of manufacturing 6-acyloxy-3,20-dioxo-1,4,6-pregnatrienes and the 1,2-dihydro analogs thereof as well as the 6-oxo-9α-halogeno-16-substituted-1,4-pregnadiene-11β,17α,21-triol-3,20-dione 17-mono- or 17,21-dihydrocarboncarboxylate intermediates useful therein which also exhibit topical anti-inflammatory activity per se.

PRIOR ART

Known in the art is 6β-acetoxyhydrocortisone 21-acetate, described as exhibiting thymolytic activity only one-third that exhibited by hydrocortisone 21-acetate. (Arch. Biochem. and Biophysics 50, 218 (1954)). Other 6β-acyloxy-4-pregnenes are described in U.S. Pat. No. 2,937,975 (column 4, lines 1-24) which discloses 6β-acyloxy-4-pregnene-17α,21-diol-3,20-diones and 16α-hydroxy analogs thereof as useful intermediates in preparing the corresponding 6β-hydroxy derivatives. Additionally, U.S. Pat. No. 2,887,499 claims 6β-acyloxy-9-unsubstituted-11-oxygenated-1,4-pregnadiene-17α,21-diol-3,20-diones and 21-alkanoates thereof which are disclosed as intermediates in preparing the corresponding 6β-hydroxy compounds and as possessing therapeutic utility per se, i.e., as pituitary inhibitors useful in the treatment of certain inflammatory diseases.

By my invention, I have produced novel 6-acyloxy-11-oxygenated-1,4,6-pregnatriene-3,20-diones and their 1,2-dihydro analogs which exhibit enhanced inflammatory activity over that exhibited by the corresponding prior art 6β-acyloxy-6,7-dihydro derivatives. This is surprising in view of prior art teaching that introduction of a 6-dehydro bond usually diminishes activity (see, e.g., M. J. Green et al, J. Steroid Biochem. 6, 599–605, May, 1975; Table 1, page 603; compare compound pairs 1,2; 6,7; 17,18; 20,21; 23,24; 26,27; 35,36; 38,39). Additionally, the 6-acyloxy-1,4,6-pregnatriene and 6-acyloxy-4,6-pregnadienes of my invention exhibit greater anti-inflammatory activity than that possessed by the corresponding 6-unsubstituted-1,4,6-pregnatriene or 6-unsubstituted-4,6-pregnadienes. This is also surprising in view of prior art teaching that introduction of a 6-acyloxy group will diminish biological activity (see, e.g., Teutsch et al, J. Med. Chem., Vol. 16, No. 12, 1371 (compound 4d) (1973) and Arch. Biochem. and Biophysics 50, 218 (1954)).

With reference to the novel 6-oxo-11-oxygenated-16-substituted-1,4-pregnadiene-3,20-diones of this invention, known in the art is 6-oxo-cortisone 21-acetate (J. Org. Chem., 27, 2544 (1962)) described as exhibiting less anti-inflammatory activity than cortisone and less than half the activity in the liver glycogen test as that exhibited by hydrocortisone. Also generically described in the art (U.S. Pat. No. 3,032,565) are other 6-oxo-9-unsubstituted-11-oxygenated-16-unsubstituted-4-pregnene-17α,21-diol-3,20-diones and esters thereof classified as valuable intermediates and as pharmacologically active substances.

By this invention, novel 6-oxo-11-oxygenated-16-substituted-1,4-pregnadiene-3,20-diones have been discovered which, in addition to being useful as intermediates in preparing the 6-acyloxy-1,4,6-pregnatrienes of this invention, also exhibit anti-inflammatory activity per se which is of about the same order as, or greater than, that of the corresponding 6-unsubstituted-1,4-pregnadienes. This is surprising in view of prior art teaching that introduction of a 6-oxygen function, specifically a 6-oxo function, diminishes biological activity (e.g. Drug Research, Vol. 5, p. 36 (1963) (Editor: Ernst Jucker); also JACS 81, 5233 (1959)). Additionally, by our invention, it has been discovered the 6-oxo-9α-halogeno-11-oxygenated-16-substituted-1,4-pregnadiene-17α,21-diol-3,20-dione 17-alkanoates and 17,21-dialkanoates exhibit excellent topical anti-inflammatory activity.

DESCRIPTION OF THE COMPOSITION-OF-MATTER ASPECT OF THE INVENTION

One of the composition-of-matter aspects of this invention resides in the concept of 3,20-dioxo-6-acyloxy-11-substituted-1,4,6-pregnatrienes and 4,6-pregnadienes having corticoid activity, particularly 6-alkanoyloxy-9α-halogenated-11-oxygenated-16-substituted-1,4,6-pregnatriene-17α,21-diol-3,20-diones 17-mono- and 17,21-dihydrocarboncarboxylates, useful as topical anti-inflammatory agents.

Typical 6-acyloxy compounds of this invention include 3,20-dioxo-6-acyloxy-1,4,6-pregnatrienes of formula I:

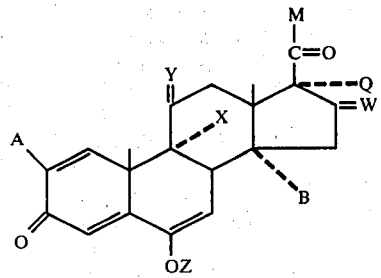

wherein
A is hydrogen or, provided Y is (H,βOH), A is chlorine, fluorine or methyl;
B is hydrogen or, together with Q, is 14α,17α-alkylidenedioxy derivative;
X is hydrogen, fluorine, or chlorine;
Y is oxygen, (H,βOH), (H,βOCOH); (H,β-chlorine) or (H,β-fluorine) provided X is chlorine;

Z is hydrocarboncarbonyl, alkoxycarbonyl, thioalkoxycarbonyl, or thioalkoxythiocarbonyl wherein Z has up to 12 carbon atoms;

Q is hydrogen provided W is (H, lower alkyl); or OV wherein V is hydrogen or an acyl radical of a hydrocarboncarboxylic acid having up to 12 carbon atoms or an acyl radical of benzoic acid substituted by a halogen or methoxy group or an acyl radical of retinoic acid provided W is other than (H,α-retinoyloxy);

W is (H, lower alkyl); (H,α-OV$_1$) wherein V$_1$ is hydrogen or an acyl radical of an acid selected from the group consisting of a hydrocarboncarboxylic acid having up to 12 carbon atoms, benzoic acid substituted by a halogen or methoxy group, retinoic acid, and isonicotinic acid; =CHT wherein T is hydrogen, lower alkyl, fluorine or chlorine; and W and Q taken together is a 16α,17α-lower alkylidenedioxy; a 16α,17α-cycloalkylidenedioxy; the grouping

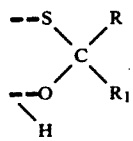

wherein R and R$_1$ are lower alkyl; or the grouping

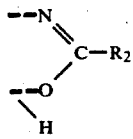

wherein R$_2$ is lower alkyl or phenyl;

M is —OR$_3$ when Q is O-acyl, R$_3$ being lower alkyl or halogeno lower alkyl; —CHO, acetals, hemiacetals and acylals thereof; —COOR$_4$ wherein R$_4$ is an alkyl group having up to 12 carbon atoms; —CH$_2$G wherein G is halogen having an atomic weight of less than 100 provided Q is not hydrogen; OV$_2$ wherein V$_2$ is hydrogen, an acyl radical of an acid selected from the group consisting of a hydrocarboncarboxylic acid having up to 12 carbon atoms, benzoic acid substituted by a halogen or methoxy group, retinoic acid, isonicotinic acid, or phosphoric acid and mono- and dialkali and alkaline earth metal salts thereof; and G together with Q is an alkylidenedioxy or an alkylorthoalkanoate; and the 1,2-dihydro analogs of the foregoing.

Alkyl groups included within the definition of W, T, R, R$_1$, R$_2$ and R$_3$ are preferably lower alkyl, particularly those having up to four carbon atoms such as methyl, ethyl, n-propyl, isopropyl, n-butyl, sec.-butyl, and tert.-butyl, although higher homologs such as pentyl and hexyl fall within the scope of this invention.

Other hydrocarbon groups contemplated for the substituent R$_4$ are aliphatic groups having up to 12 carbon atoms including straight and branched chain alkyl groups and cycloaliphatic groups which can be saturated or unsaturated, substituted or unsubstituted; aryl, aralkyl, and alkaryl groups. Of the foregoing, preferred are alkyl groups having up to four carbon atoms. Typical unsaturated aliphatic groups are vinyl, propenyl, propynyl, and butenyl; typical cycloalkyl groups are cyclopropyl, cyclopentyl, cyclohexyl, cyclopentenyl, and p-dicyclohexyl; typical aryl groups are phenyl, α-naphthyl, and p-diphenyl; typical alkaryl groups are tolyl, xylyl, and symdiethylphenyl; and typical aralkyl groups are benzyl, phenethyl and diphenylmethyl.

As used in the specification and claims of this application, the term "acyl" denotes a radical derived from an acid by removal of a hydroxyl group; e.g., acetyl is the acyl radical of acetic acid, benzenesulfonyl is the acyl radical of benzenesulfonic acid, benzoyl is the acyl radical of benzoic acid, and ethoxycarbonyl is the acyl radical of ethylcarbonic acid.

The acyl radicals of the compounds of this invention as defined by V, V$_1$ and V$_2$ in formula I hereinabove include those derived from hydrocarboncarboxylic acids having up to 12 carbon atoms which may be saturated, unsaturated, straight chain or branched chain, aliphatic, cyclic, cyclic-aliphatic, aromatic, aryl-aliphatic, or alkyl-aromatic, and may be substituted by hydroxy, alkoxy containing from 1 to 5 carbon atoms or by a halogen. Typical ester groups at the 16, 17, and/or 21-positions of the 6-acyloxy-3,20-dioxo-1,4,6-pregnatrienes of my invention are thus derived from hydrocarboncarboxylic acids such as alkanoic acids exemplified by acetic, propionic, trimethylacetic, butyric, isobutyric, valeric, isovaleric, caproic, tert.-butylacetic, enanthic, caprylic, capric, cyclopentylpropionic, undecylic, lauric, and adamantanecarboxylic acids; substituted alkanoic acids such as phenoxyacetic, trifluoroacetic, and β-chloropropionic acids; aromatic and substituted aromatic acids including benzoic, toluic, isonicotinic, p-chlorobenzoic, p-fluorobenzoic, p-methoxybenzoic, and 3',5'-dimethylbenzoic acids; aryl-alkanoic acids such as phenylacetic, phenylpropionic, and β-benzoylaminoisobutyric acids; unsaturated acids such as acrylic, sorbic and retinoic acids; dibasic acids such as succinic, tartaric, phthalic and benzene disulfonic acids.

The term "lower alkanoyloxy" is contemplated as including acid radicals of lower alkanoic acids having preferably up to 8 carbon atoms such as radicals obtained from acetic, propionic, butyric, valeric, caprylic, caproic, tert.-butylacetic acid and the like.

The hydrocarboncarbonyl radicals defined by "Z" include those derived from hydrocarboncarboxylic acids having up to 12 carbon atoms encompassed within the terms V, V$_1$ and V$_2$ discussed hereinabove. Also included within the term "Z" are alkoxycarbonyl groups having up to 12 carbon atoms including ethoxycarbonyl, propyloxycarbonyl, hexyloxycarbonyl, decyloxycarbonyl; thioalkoxycarbonyl groups such as thioethoxycarbonyl, or thioheptyloxycarbonyl; and thioalkoxythiocarbonyl groups such as thioethoxythiocarbonyl.

The halogens at C-21 as defined by G in above formula I are bromine, chlorine and fluorine. Of the halogens at C-9, preferred is fluorine.

The alkylidene groups contemplated in the compounds of our invention are preferably lower alkylidenes, i.e., hydrocarbon radicals having preferably up to 4 carbon atoms including radicals such as methylene, ethylidene, n-propylidene, isopropylidene, n-butylidene, and sec.-butylidene and the like. The 16-lower alkylidene derivatives of this invention (i.e. when W in above formula I is =CHT) are double bonded to the D ring at C-16. The 16α,17α-alkylidenedioxy derivatives have the alkylidene terminal bonds attached to different oxygen atoms, i.e., to the oxygens at C-16 and C-17 in the case of the 16α,17α-alkylidenedioxy derivatives, to oxygens at C-17 and C-21 in the case of the 17α,21- alkylidenedioxy derivatives, and to oxygens at C-14 and C-17 in the case of the 14α,17α-alkylidenedioxy derivatives.

Of the pregnadieno(17,16α-d)-1,3-oxythiolanes of my invention (i.e., compounds of formula I wherein W and Q together form the grouping

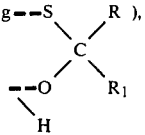

), preferred are those wherein R and $R_1$ are both methyl groups.

Of the 5'βH-pregnadieno(17,16-d)oxazoline -3,20-diones of my invention (i.e., compounds of formula I wherein W and Q together form the grouping

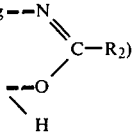

)

preferred are those wherein $R_2$ is methyl.

The physical embodiments of the 6-acyloxy-3,20-dioxo-1,4,6-pregnatrienes and 4,6-pregnadienes of this invention are characterized by being crystalline solids, usually white to off-white in color which are insoluble in water (with the exception of alkali metal salts of esters such as the hemisuccinate and phosphate esters thereof) and soluble in most organic solvents, particularly in acetone, dioxane, dimethylformamide, and dimethylsulfoxide, although of limited solubility in non-polar solvents such as dialkylethers and alkylhydrocarbons.

In general, the 6-acyloxy-1,4,6-pregnatrienes and 6-acyloxy-4,6-pregnadienes of my invention, particularly those of formula I wherein G is hydroxy, acyloxy, or together with Q is a 17α,21-alkylidenedioxy, exhibit corticosteroid activity. Of these, both those which have halogens at both C-9 and C-11 and those having an oxygen function at C-11 and a hydrogen or halogen at C-9, possess glucocorticoid activity and are particularly valuable as anti-inflammatory agents. Of the foregoing, preferred anti-inflammatory agents (particularly when administered topically) are 3,20-dioxo-6-acyloxy-16-substituted-1,4,6-pregnatriene-17α,21-diols having a 9α-halogen (preferably 9α-fluoro-), an 11β-hydroxyl function and an ester function at C-17. Of these, the 3,20-dioxo-6-acyloxy-9α-halogeno-11β-hydroxy-16-methyl-1,4,6-pregnatriene-17α,21-diol 17-mono- and 17,21-diesters are particularly useful as topical anti-inflammatory agents. Of the foregoing, preferred are those wherein said 6-acyloxy is a hydrocarboncarbonyl having up to eight carbon atoms, particularly 6-lower alkanoates such as 6-acetate and 6-propionate.

Thus, compounds of this invention which are particularly useful as topical anti-inflammatory agents are the 6-hydrocarboncarbonyl derivatives of formula I having a cortical side chain at C-17 (i.e., compounds of formula I wherein M is $CH_2OV_2$ and Q is OV (V being an acyl radical), particularly compounds unsubstituted at C-2 and at C-14. Of these, the 1,4,6-pregnatrienes of formula I having a 9α-fluoro or 9α-chloro group and having a 16-substituent, e.g., 16-methylene, 16α,17α-isopropylidenedioxy, and, preferably, a 16-methyl group, exhibit excellent topical anti-inflammatory activity superior to the topical anti-inflammatory activity of the corresponding 6-unsubstituted-1,4,6-pregnatriene or to that of the corresponding 6-acyloxy-1,4-pregnadiene. Particularly valuable compounds of our invention are 6-hydrocarbonyloxy-3,20-dioxo-1,4,6-pregnatrienes of formula II:

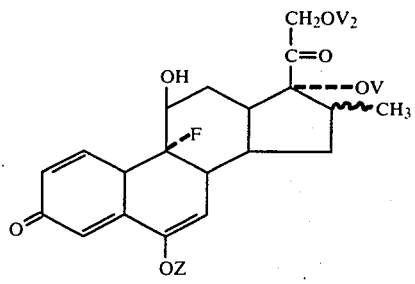

wherein
V and $V_2$ are each hydrogen or an acyl radical of a hydrocarboncarboxylic acid having up to 12 carbon atoms; and
Z is a hydrocarboncarbonyl having up to eight carbon atoms.

Compounds of formula II wherein V alone or both V and $V_2$ are hydrogen are useful systemic anti-inflammatory agents, and are also valuable as intermediates in preparing the preferred 17-mono- and 17,12-diester topical anti-inflammatory compounds of formula II.

Of the compounds of formula II, particularly useful topical anti-inflammatory agents are those wherein at least V is an acyl radical of a hydrocarboncarboxylic acid having up to 8 carbon atoms, particularly the 17-propionate and 17-isobutyrate derivatives which exhibit high topical anti-inflammatory activity with low systemic corticoid effects. When administered topically, it has been discovered that the ester groups at C-17 appears to have a much greater effect on the topical anti-inflammatory activity of the compounds of this invention than the ester groups at C-6 and/or at C-21 so that the topical activity of a 6,17,21-tripropionate derivative of formula II will not be changed to any great extent by the presence at C-6 and/or at C-21 of other hydrocarboncarboxylic acid esters. The 16β-methyl-17,21-diacyl derivatives of formula II are most valuable, having enhanced topical activity over that possessed by the corresponding 6-unsubstituted analogs or by the corresponding 6β-acyloxy-6,7-dihydro analogs. Of these, the 17-propionate 6,21-dilower alkanoates and 17-isobutyrate 6,21-dilower alkanoates are preferred species.

The superior topical activity of the 3,20-dioxo-6,17-diacyloxy-9α-fluoro-16-methyl-1,4,6-pregnatrienes of formula II, particularly the 16β-methyl derivatives thereof, are demonstrated by pharmacological tests in animals. Thus, for example, when tested in mice by a modification of the croton oil-induced ear edema test (G. Tonelli et al, Endocrinology 77, 625-634 (1965)), 6-acetoxy-9α-fluoro-16β-methyl-1,4,6-pregnatriene-11β, 17α, 21-triol-3,20-dione 17,21-dipropionate exhibits topical anti-inflammatory activity about four times greater than that exhibited by the corresponding 6-unsubstituted derivative and over eight times greater than the topical anti-inflammatory activity of the corresponding 6β-acyloxy-6,7-dihydro analog. Similarly, the corresponding 9α-chloro compound, i.e., 6-acetoxy-9α- chloro-16β-methyl-1,4,6-pregnatriene-11β, 17α,21-triol-3,20-dione 17,21-dipropionate, exhibits topical antiinflammatory activity which is about three times greater than that exhibited by the corresponding 6-unsubstituted derivative.

Preferred compounds of formula II include the 6-acetate, 6-propionate and 6-benzoate of 9α-fluoro-16β-methyl-1,4,6-pregnatriene-6,11β,17α,21-tetrol-3,20-dione 17,21-dipropionate, of 9α-fluoro-16β-methyl-1,4,6-pregnatriene-6,11β,17α,21-tetrol-3,20-dione 17-propionate 21-acetate, and of 9α-fluoro-16β-methyl-1,4,6-pregnatriene-6,11β,17α,21-tetrol-3,20-dione 17-isobutyrate 21-propionate, and the 9α-chloro analogs thereof.

Of the foregoing, particularly valuable are the 6,17,21-tripropionate and the 6,21-dipropionate 17-isobutyrate of 9α-fluoro-16β-methyl-1,4,6-pregnatriene-6,11β,17α,21-tetrol-3,20-dione, and the 6-acetate 17,21-dipropionate of 9α-chloro-16β-methyl-1,4,6-pregnatriene-6,11β, 17α,21-tetrol-3,20-dione, all of which have high topical and local anti-inflammatory activity equal to or greater than that exhibited by betamethasone 17-valerate (i.e., 9α-fluoro-16β-methyl-1,4-pregnadiene-11β,17α,21-triol-3,20-dione 17-valerate), coupled with low systemic effects following topical applications.

In addition to the preferred compounds of formula II, this invention includes 6-acyloxy-1,4,6-pregnatrienes of formula I wherein said 6-acyloxy is an alkoxycarbonyl, a thioalkoxycarbonyl, or a thioalkoxythiocarbonyl, e.g., the 6-ethylcarbonate 17,21-di-propionate, the 6-thioethylcarbonate 21-acetate, and the 6-thioethylthiocarbonate 17,21-dipropionate, respectively, of 9α-fluoro-16β-methyl-1,4,6-pregnatriene-6,11β,17α,21-tetrol-3,20-dione;

9-unsubstituted derivatives of formula I;

9α,11β-dihalogeno pregnatrienes of formula I (i.e., wherein X and Y are both halogen) such as:

9α,11β-dichloro-16α-methyl-1,4,6-pregnatriene-6,17α,21-triol-3,20-dione 6-propionate 21-acetate; 9α,11β-dichloro-16β-methyl-1,4,6-pregnatriene-6,17α,21-triol-3,20-dione 6,17,21-tripropionate and n-butyl 6-hydroxy-9α-chloro-11β-fluoro-14α,17α-ethylidenedioxy-3,20-dioxo-1,4,6-pregnatrien-21-oate 6-acetate;

21-halogeno pregnatrienes (i.e., compounds of formula I wherein M is CH₂G, G being halogen) such as:

21-chloro-16-methylene-1,4,6-pregnatriene-6,11β,17α-triol-3,20-dione 6,17-dipropionate and the corresponding 16β-methyl derivative thereof; and 21-fluoro-16β-methyl-1,4,6-pregnatriene-6,11β,17α-triol-3,20-dione 6,17-dipropionate;

16α-hydroxy pregnatrienes (i.e., compounds of formula I wherein W is (H,α—OH)) and derivatives thereof such as 9α-fluoro-1,4,6-pregnatriene-6,11β,16α,17α,21-pentol-3,20-dione as the 17-propionate, the 16,21-diacetate 17-propionate, and the 16α,17α-cyclopentylidenedioxy 21-acetate esters thereof and as the 16α,17α-isopropylidenedioxy 21-acetate derivative thereof;

[17,16α-d]-1′,3′-oxathiolane derivatives (i.e., compounds of formula wherein N and Q together form

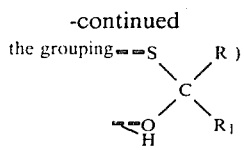

such as:

6-acetoxy-9α-fluoro-11β,21-dihydroxy-2′,2′-dimethyl-1,4,6-pregnatrieno-[17,16α-d]-1′,3′-oxathiolane-3,20-dione 21-propionate;

5′βH-pregnadieno[17,16α-d]oxazolines (i.e., compounds of formula I wherein W and Q together form the grouping —N⫽C—R₂)

such as:

9α-fluoro-6,11β,21-trihydroxy-2′-methyl-5′βH-1,4,6-pregnatrieno[17,16α-d]oxazoline-3,20-dione 6,21-diacetate;

20-carboxylate pregnatrienes (i.e., compounds of formula I wherein M is —COOR₄, R₄ being a hydrocarbon group such as n-butyl 9α-fluoro-6,11β-dihydroxy-3,20-dioxo-16α,1-7α-isopropylidenedioxy-1,4,6-pregnatrien-21-oate 6-acetate;

propyl 2-chloro-6,11β-dihydroxy-3,20-dioxo-16α-methyl-1,4,6-pregnatrien-21-oate 6-acetate;

20-alkoxy-21-nor pregnatrienes (i.e., compounds of formula I wherein M is —OR₃, R₃ being alkyl or halogenoalkyl) (also may be termed as alkyl androstatriene-17β-carboxylates) such as:

9α-fluoro-16β-methyl-20-chloromethoxy-21-nor-1,4,6-pregnatriene-6,11β,17α-triol-3,20-dione 6-acetate 17-propionate;

16β-methyl-20-methoxy-21-nor-1,4,6-pregnatriene-6,11β,17α-triol-3,20-dione 6-acetate 17-propionate;

21-oxo pregnatrienes and derivatives thereof (i.e., compounds of formula I wherein M is —CHO, and acetals, hemiacetals and acylals thereof) such as:

2-chloro-9α-fluoro-16α-methyl-1,4,6-pregnatriene-6,11β,17α-triol-3,20,21-trione 6-acetate and the 21-methylhemiacetal thereof;

9α-fluoro-16α-methyl-21,21-diacetoxy-1,4,6-pregnatriene-6,11β,17α-triol-3,20-dione 6-acetate 17-propionate;

9α-fluoro-16α-methyl-1,4,6-pregnatriene-6,11β,17α-triol-3,20,21-trione 6,17-dipropionate and the 21-ethylene ketal and the 21,21-dimethylacetal thereof;

and the 1,2-dihydro analogs of the foregoing such as:

9α-fluoro-16β-methyl-4,6-pregnadiene-6,11β,17α,21-tetrol-3,20-dione 6,17,21-tripropionate and the corresponding 9α-chloro derivative.

Another composition-of-matter aspect of this invention resides in the concept of 3,6,20-trioxo-1,4-pregnadienes of the formula III:

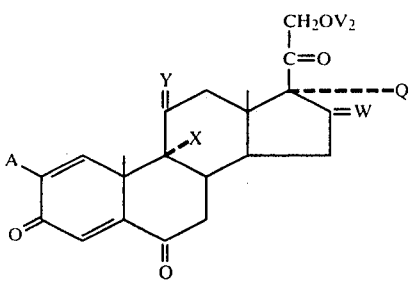

wherein

A is hydrogen or chloro;

X is hydrogen, fluorine or chlorine;

Y is (H,βOH) or (H,β-chlorine) provided X is chlorine;

Q is hydroxy or OV wherein V is an acyl radical of a hydrocarboncarboxylic acid having up to 8 carbon atoms;

$V_2$ is hydrogen or an acyl radical of a hydrocarboncarboxylic acid having up to 8 carbon atoms, and $OV_2$ together with Q is alkylidenedioxy or alkylorthoalkanoate;

W is (H,CH₃), methylene, (H,αOV₂) wherein $V_2$ is as hereinabove defined;

or together, W and Q form an alkylidenedioxy group or the grouping

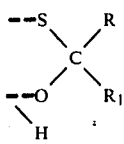

wherein R and $R_1$ are lower alkyl; or the grouping

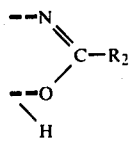

wherein $R_2$ is lower alkyl or phenyl.

The compounds of formula III, in addition to being useful as intermediates in preparing the corresponding 6-acyloxy-1,4,6-pregnatrienes of formula I, unexpectedly also exhibit high topical anti-inflammatory activity per se. Of the compounds of formula III, preferred are the 9α-fluoro-11β-hydroxy-16-methyl-17α,21-diols and esters thereof of the following formula IV:

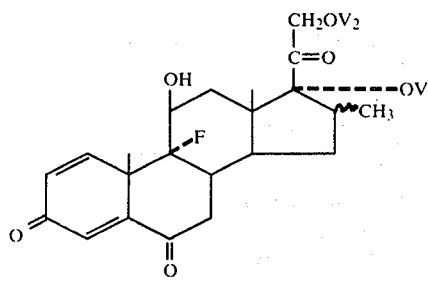

wherein V and $V_2$ are as hereinabove defined for formula III.

In general, the 16β-methyl derivatives of formula IV are preferred, particularly the 17,21-dipropionate, and the 17-isobutyrate and 17-valerate esters thereof, which exhibit topical activity greater than that of betamethasone 17-valerate, the latter two also exhibiting activity much greater than that of the corresponding 6-desoxy compounds when tested in animals via the well-known mouse croton ear assay. Another particularly valuable compound of formula IV is the 17-isobutyrate of 6-oxo-dexamethasone (i.e., 9α-fluoro-16α-methyl-1,4-pregnadiene-11β,17α,21-triol-3,6,20-trione 17-isobutyrate); while a valuable compound of formula III is 9α-fluoro-16α,17α-isopropylidenedioxy-1,4-pregnadiene-11β,21-diol-3,6,20-trione 21-acetate. Both the foregoing compounds, exhibit greatly enhanced topical activity over that exhibited by betamethasone 17-valerate or the corresponding 6-desoxy-1,4-pregnadienes. This is surprising when one considers the teaching in the art (discussed hereinabove) that introduction of a 6-oxygenated function diminishes biological activity.

PROCESS OF THE INVENTION

The 6-acyloxy-3,20-dioxo-1,4,6-pregnatrienes and 4,6-pregnadienes of this invention wherein said acyl group is an acid radical of an acid selected from the group consisting of a hydrocarboncarboxylic acid, an alkylcarbonic acid, an alkylthiocarbonic acid and an alkyldithiocarbonic acid, said acid radical having up to 12 carbon atoms, are conveniently prepared by the treatment of a 3,6-dioxo-1,4-pregnadiene or of a 3,6-dioxo-4-pregnene under esterification conditions, preferably with an acid anhydride or an acid halide of said acid in a tertiary amine.

In brief, in a preferred mode of my process, when a 3,6-dioxo-1,4-pregnadiene (or a 3,6-dioxo-4-pregnene) is subjected to a basic esterification medium (e.g., acetic anhydride in pyridine) enolization to the corresponding 3-oxo-6-hydroxy-1,4,6-pregnatriene (or 4,6-pregnadiene) occurs in situ with concomitant esterification at C-6. Thus, when 6-oxo-betamethasone 17,21-dipropionate (i.e., 9α-fluoro-16β-methyl-1,4-pregnadiene-11β,17α,21-triol-3,6,20-trione 17,21-dipropionate) is treated with an acid anhydride (i.e., acetic anhydride) or an acid halide (e.g., benzoyl chloride) in a tertiary amine (usually pyridine) there is obtained the corresponding 6-acyloxy-1,4,6-pregnatriene, e.g., the 6-acetate or 6-benzoate, respectively, of 9α-fluoro-16β-methyl-1,4,6-pregnatriene-6,11β,17α,21-tetrol-3,20-dione 17,21-dipropionate.

The acid anhydride and acid halide reagents of my process are derived from hydrocarboncarboxylic acids having up to 12 carbon atoms, including those derived from alkanoic acids exemplified by acetic, propionic, trimethylacetic, butyric, isobutyric, valeric, isovaleric, caproic, tert.-butylacetic, enanthic, caprylic, capric, cyclopentylpropionic, undecylic, lauric, and adamantanecarboxylic acids; from aromatic acids including benzoic, toluic and 3',5'-dimethylbenzoic acids; and from arylalkanoic acids such as phenylacetic and phenylpropionic. Other acid halide reagents of this process include those derived from alkylcarbonic acids (e.g., ethylchloroformate, also named ethylchlorocarbonate), alkylthiocarbonic acids (e.g., ethylchlorothiolformate), and alkyldithiocarbonic acids (e.g., ethylchlorodithioformate).

Tertiary amines useful in my process include trialkyl amines such as trimethylamine and tripropylamine, and cyclic tertiary amines such as pyridine and picolines.

Preferred for use in my process is pyridine together with an acid halide or acid anhydride of a lower alkanoic acid having up to 3 carbon atoms, e.g., acetyl chloride or propionic anhydride.

Usually, it is not necessary to use a solvent other than the acid reagent and tertiary amine. However, if desired, an anhydrous non-reactive organic solvent may be used in carrying out our process. By "non-reactive" is meant any organic solvent which will not react with the steroid substrate or acid reagents which would cause transformations resulting in competing side reactions. Thus, in this process, solvents to be avoided are water and alcohols (which will react with reagents) and nitriles such as acetronitrile (which would form iminoethers with steroidal alcohols).

Substituents present in the 3,6,20-trioxo-1,4-pregnadiene and 4-pregnene starting steroids of our process usually remain unchanged under the conditions of my process. Indeed, it is usually preferable to have all the substituents desired in the 6-acyloxy-3,20-dioxo-1,4,6-pregnatriene (or 4,6-pregnadiene) product present in the 3,6,20-trioxo-1,4-pregnadiene (or 4-pregnene) starting compound. Thus, by way of example, the 3,6,20-trioxo-1,4-pregnadiene (or 4-pregnene) starting steroids of my process may be substituted at C-2 by methyl or halogen; at C-9 by fluorine or chlorine; at C-11 by oxygen, hydroxyl, formyloxy or halogen; at C-16 by acyloxy, alkyl, alkylidene, halogenoalkylidene; and at C-17 there may be present a corticoid side chain or derivative thereof, or a progesterone side chain substituted by a 17α-hydroxy or 17α-acyloxy and substituted at C-21 by acyloxy, alkoxy, halogen, oxygen or derivatives thereof.

Hydroxyl groups present at C-16 and/or C-21 will be acylated under the reaction conditions of this process. If such acylation is not desired, it is necessary to protect the 16 and/or 21-hydroxyl group by protection procedures well known in the art such as those utilizing dimethyl-t-butyl silyl chloride or triethylmethoxyethoxymethylammonium chloride or allyl chloride whereby are prepared the corresponding ether derivatives, i.e. the 16 and/or 21-dimethyl-t-butylsilyl ether or the methoxyethoxymethyl ether or the 21-allyl ether, all of which, after introduction of the 6-acyloxy-6-dehydro system, may be cleaved via known methods without removing the 6-acyloxy group to form a 6-acyloxy-3,20-dioxo-1,4,6-pregnatriene or 4,6-pregnadiene of formula I having 16 and/or 21-hydroxyl groups which, in turn, may be esterified with acyl groups different than the 6-acyloxy function utilizing standard esterification techniques.

In addition, a 21-hydroxyl group may be protected via a 17α,21-alkylorthoalkanoate which may be cleaved by mild acid hydrolysis (e.g., aqueous acetic acid at room temperature) after introduction of the 6-acyloxy-6-dehydro system, to form a 6,17α-diacyloxy-21-hydroxy-3,20-dioxo-1,4,6-pregnatriene of this invention.

Additionally, under the conditions of the reaction a 21-aldehyde group will be converted to a 21-acylal function. Thus, in preparing a 6-acyloxy-3,20-dioxo-1,4,6-pregnatriene or 4,6-pregnadiene having a 21-aldehyde function, it is usually preferable to first prepare a 6-acyloxy-3,20-dioxo-1,4,6-pregnatriene or 4,6-pregnadiene having a 21-hydroxyl function in the manner described above and thence oxidize the 21-hydroxyl group utilizing oxygen and cupric acetate in known manner to obtain the desired 21-aldehyde derivative of formula I.

Generally, when carrying out my process, there is added to a 6-oxo-4-pregnene starting compound (e.g. 9α-fluoro-16β-methyl-1,4-pregnadiene-11β,17α,21-triol-3,6,20-trione 17,21-dipropionate) in a tertiary amine (usually pyridine) either an acid anhydride (e.g. acetic anhydride) or acid halide (e.g. benzoyl chloride), the molar quantity of acid reagent being in excess to that of steroid starting compound. The reaction is usually carried out at room temperature until complete as determined by thin layer chromatography or ultraviolet spectroscopy. The reaction is usually completed in about 4 hours. When using an anhydride or halide of a hindered acid such as a secondary or tertiary acid (e.g., trimethylacetic acid), it may be necessary to use more vigorous conditions such as heating or using a catalyst (e.g., 4-N,N-dimethylaminopyridine) or longer reaction time. The resulting 6-acyloxy-1,4,6-pregnatriene (e.g., 9α-fluoro-16β-methyl-1,4,6-pregnatriene-6,11β,17α,21-tetrol-3,20-dione 6-acetate or 6-benzoate 17,21-dipropionate) is conveniently isolated and purified by pouring the reaction solution into dilute acid (e.g., hydrochloric), separating the resulting precipitate by filtration or by extraction with organic solvents, and purifying via crystallization and/or chromatographic techniques.

When carrying out the foregoing process on a 3,6-dioxo-1,4-pregnadiene (or 3,6-dioxo-4-pregnene) containing a free 21-hydroxyl group using a bulky acid chloride or acid anhydride (e.g., trimethylacetic anhydride), there may be obtained the intermediate 3,6-dioxo-1,4-pregnadiene (or 3,6-dioxo-4-pregnene) 21-ester if the reaction is terminated too soon.

An alternate method of preparing a 9-unsubstituted-6-acyloxy-3,20-dioxo-4,6-pregnadiene of forumla I is to reduce the corresponding 1,4,6-pregnatriene by methods which will not affect the 6-acyloxy function, e.g., by hydrogenation in the presence of tris-triphenylphosphine rhodium chloride. Conversely, a 6-acyloxy-3,20-dioxo-1,4,6-pregnatriene of formula I may be prepared from the corresponding 4,6-pregnadiene by methods known to introduce a 1-dehydro bond while not affecting the 6-acyloxy function, e.g., methods such as those utilizing selenium dioxide or 2,3-dichloro-5,6-dicyanobenzoquinone (DDQ) and hydrogen chloride.

The conversion of a 3,6-dioxo-1,4-pregnadiene (or 3,6-dioxo-4-pregnene) to a 6-acyloxy-3-oxo-1,4,6-pregnatriene may also be carried out utilizing other esterification media, e.g., an acid anhydride or acid halide in the presence of a strong acid (e.g., p-toluenesulfonic acid or perchloric acid), optionally with an added inert solvent. Under these conditions, however, any hydroxyl group at C-11 will be esterified in addition to those at C-16 and C-21.

I have discovered when preparing 6-acyloxy-6-dehydro compounds of formula I that a 6-dehydro bond cannot be introduced into either a 6β-hydroxy- or -6β-acyloxy-1,4-pregnadiene or 4-pregnene by standard methods known to introduce a 6-dehydro bond such as that utilizing DDQ and hydrogen chloride.

I have also discovered that when a 6-acyloxy-3,20-dioxo-1,4-pregnatriene or 4,6-pregnadiene of formula I is subjected to a basic or strongly acid hydrolytic medium, there is obtained a 3,6,20-trioxo-1,4-pregnadiene or 4-pregnene rather than the corresponding 6-hydroxy-3,20-dioxo-1,4,6-pregnatriene or 4,6-pregnadiene. Thus, the 6-acyloxy-6-dehydro compounds of my invention are trapped enol derivatives which are basically different from the prior art 6-acyloxy-6,7-dihydro esters which, upon hydrolysis, are converted to their corresponding 6-hydroxyl derivatives.

The 3,6,20-trioxo-1,4-pregnadiene and 3,6,20-trioxo-4-pregnene intermediates of this invention including the preferred topical anti-inflammatory agents of formulae III and IV may be prepared via procedures analogous to known methods for introducing an oxo group. I prefer to utilize procedures similar to those described by Pfitzner and Mofiatt, J. Am. Chem. Soc., 87:24 (5670–5678 (1965)) whereby a 6$\beta$-hydroxyl-3,20-dioxo-1,4-pregnadiene or a 6$\beta$-hydroxyl-3,20-dioxo-4-pregnene is converted to the corresponding 6-oxo derivative by reaction in dimethylsulfoxide and an inert solvent (e.g., benzene) with about three moles of dicyclo-hexylcarbodiimide in the presence of equimolar quantities of a tertiary amine (usually pyridine) and a strong acid (e.g., trifluoroacetic acid), the molar quantities of tertiary amine and acid being about equivalent to that of starting 6$\beta$-hydroxy steroid.

In the foregoing procedure, it is necessary that any hydroxyl group at C-16 and/or 21 be protected such as by an ester derivative prior to conversion of the 6$\beta$-hydroxyl derivative to the corresponding 6-oxo derivative. Any 6-oxo-16 and/or 21-acyloxy derivative thereby prepared may then be converted to the corresponding 6-oxo-16 and/or 21-hydroxy compound utilizing standard procedures such as that utilizing aqueous sodium bicarbonate. The 3,6,20-trioxo-1,4-pregnadiene (or 4-pregnene)-17$\alpha$,21-diols may then be converted to a 17$\alpha$,21-orthoester in known manner and thence, upon hydrolysis with acetic acid to a 17-monoester of formulae III or IV, sometimes coproduced with some 21-monoester, said derivatives being separable by chromatographic techniques. The 3,6,20-trioxo-1,4-pregnadiene 17,21-diesters of formulae III and IV are best prepared by oxidation of the appropriate 6-hydroxy-3,20-dioxo-1,4-pregnadiene 17,21-diesters.

The requisite 6$\beta$-hydroxy-1,4-pregnadiene and 6$\beta$-hydroxy-4-pregnene precursors of the corresponding 6-oxo intermediates are either known compounds or are prepared according to procedures known in the art. The 6$\beta$-hydroxy-1,4-pregnadiene precursors, including those to the preferred compounds of formulae II and IV, are conveniently prepared by converting the corresponding 6-unsubstituted-1,4-pregnadiene (e.g. betamethasone 21-acetate) to the corresponding enol benzoate (e.g. 9$\alpha$-fluoro-16$\beta$-methyl-1,3,5-pregnatriene-3,11$\beta$, 17$\alpha$, 21-tetrol-20-one 3-benzoate 21-acetate) by reaction with benzoyl chloride in dry pyridine followed by reaction of the resulting enol benzoate with oxygen in a halogenated solvent.

THE METHOD OF USE AND PHARMACEUTICAL FORMULATION ASPECTS OF THE INVENTION

The present invention includes within its scope the method of treating an inflammatory condition in a warm-blooded animal responsive to treatment with anti-inflammatory agents which comprises administering to said animal a non-toxic, anti-inflammatory effective amount of a 6-acyloxy-3,20-dioxo-1,4,6-pregnatriene or 4,6-pregnadiene of formula I.

In general, the pharamcologically active 6-acyloxy-3,20-dioxo-1,4,6-pregnatrienes and 4,6-pregnadienes of formula I have pharamacological effects similar to those of the corresponding 6-unsubstituted analog and may be administered in similar pharmaceutical forms and for the same indications for which the corresponding 6-unsubstituted-3,20-dioxo-1,4,6-pregnatriene or 4,6-pregnadiene would be applicable, the total daily dosage depending upon the nature and severity of the inflammation being treated, the age and size of the patient and the specific potency of the 6-acyloxy-3,20-dioxo-1,4,6-pregnatriene or 4,6-pregnadiene being administered. Thus, in general, 6-acyloxy-3,20-dioxo-1,4,6-pregnatrienes and 4,6-pregnadienes of formula I may be administered orally in the form of tablets, elixirs, capsules and the like for all inflammatory disorders, particularly arthritis, rheumatism and the like; intravenously in aqueous solution as the 21-hemisuccinate or 21-phosphate ester for the treatment of shock and intramuscularly for long-term systemic activity.

In particular, the 6-acyloxy-3,20-dioxo-1,4,6-pregnatrienes and 4,6-pregnadienes of formula I having an ester group at C-17 and a hydroxy or ester thereof at C-21 (i.e., compounds of formula I wherein Q is O-acyl and M is —CH$_2$OV$_2$), and more particularly, the preferred compounds of formula II, are valuable anti-inflammatory agents when administered topically, or locally, since they have high anti-inflammatory action coupled with low glucocorticoid action on topical administration. The compounds thus have the desirable high anti-inflammatory action on topical administration with low risk of disturbance of the mineral balance or other systemic action should the compound be absorbed.

The 6-acyloxy-3,20-dioxo-17$\alpha$, 21-dihydroxy-1,4,6-pregnatrienes (and 4,6-pregnadienes ) 17-mono esters and 17,21-diesters thereof may be applied topically or locally in any of the conventional pharmaceutical forms. For example, they may be administered intra-articularly for long-term local activity with minimal systemic effects in aqueous suspensions as the 6,17,21-trihydrocarboncarboxylate esters, e.g., the 6,17,21-tripropionate, 6,21dipropionate 17-isobutyrate, and 6-acetate 17,21-dipropionate, or topically in creams, lotions, aerosols, or ointments as the 6$\beta$17$\alpha$-dialkanoates or as the 6$\beta$-alkanoate-17$\alpha$-benzoate or as the 6$\beta$,17$\alpha$, 21-trialkanoates (e.g., 6$\beta$,17$\alpha$,21tripropionate) in the treatment of all corticosteroid responsive dermatoses such as contact and allergic dermatitis and psoriasis or in the form of ophthalmic suspensions or nasal sprays. Advantageously, when topically administering preferred compounds of our invention, e.g., 9$\alpha$-fluoro- and 9$\alpha$-chloro-6-acyloxy-3,20-dioxo-16-methyl-1,4,6-pregnatrienes of formula II, and particularly the 6,17,21-trihydrocarboncarboxylates thereof, the therapeutic topical dosages will generally be lower than those required when administering the corresponding 6-unsubstituted analogs or the corresponding 6$\beta$-acyloxy-6,7-dihydro derivatives. Thus, a preferred mode of the method-of-use aspect of my invention comprises the method of treating a topical inflammatory condition, e.g., inflammation of the skin or mucous membrane, which comprises topically applying to the affected area in a concentration effective for the topical treatment of inflammation of a 6-acyloxy-3,20-dioxo-1,4,6-pregnatriene of formula II in association with a pharmaceutical carrier.

Included within the term "topically applying" are topical application on skin whereby my compounds of formula II are effective in the treatment and control of all corticosteroid-responsive dermatoses, e.g., psoriasis; inhalation aerosol application whereby my preferred compounds of formula II are effective in the treatment of, e.g., respiratory inflammatory disorders such as asthma and allergic rhinitis; and intra-articular injection application whereby my preferred compounds of formula II are effective in the treatment of local inflammatory disorders such as rheumatoid arthritis, tennis elbow, bursitis, peritendinitis, capsulitis, gout, and acute shoulder dermatitis.

Particularly valuable compounds of formula II for the topical treatment of inflammatory disorders are the 9α-halogeno-16β-methyl-6,17α,21-trihydrocarboncarboxylates such as the 6,17α,21-tripropionate or the 6-acetate 17,21-dipropionate or the 6,21-dipropionate 17-isobutyrate of 9α-fluoro-16β-methyl-1,4,6-pregnatriene-6,11β, 17α,21-tetrol-3,20-dione and the 6,21-diacetate of 9α-fluoro-16α,17α-isopropylidenedioxy-1,4,6-pregnatriene-6,11β,21-triol-3,20-dione, each of which has greater topical activity than the corresponding 6-unsubstituted precursor or 6β-acyloxy-1,4-pregnadiene, most of them exhibiting a topical activity about equal to or greater than betamethasone 17-valerate (i.e. 9α-fluoro-16β-methyl-1,4-pregnadiene-11,β,17α,21-triol-3,20-dione 17-valerate) and also exhibiting low systemic effects following topical application.

Another method-of-use aspect of this invention resides in the concept of the method of treating an inflammatory condition in a warm-blooded animal which comprises administering to said animal a non-toxic, anti-inflammatory active amount of a 3,6,20-trioxo-1,4-pregnadiene of formula III hereinabove, together with a non-toxic, pharmaceutically acceptable carrier.

In general, the 3,6,20-trioxo-1,4-pregnadienes of formula III have pharmacological effects similar to the corresponding 6-unsubstituted analog and may be administered in similar pharmaceutical forms and for the same indications for which the corresponding 6-unsubstituted-1,4-pregnadiene would be applicable, the total daily dosage and dosage forms being dependent upon the same indications and being similar to those described hereinabove for the 6-acyloxy-1,4,6-pregnatrienes of formula I.

The most useful 3,6,20-trioxo-1,4-pregnadienes are the 16-methyl-3,6,20-trioxo-1,4-pregnadienes of formula IV having an ester function at C-17, particularly the 16β-methyl derivatives and those discussed hereinabove in the composition-of-matter section which are valuable anti-inflammatory agents when administered topically or locally since they have a high anti-inflammatory action coupled with low glucocorticoid action on topical administration. Advantageously, when administering the preferred 6-oxo-16-methyl pregnadienes of formula IV and the valuable 9α-fluoro-16α,17α-isopropylidenedioxy-1,4-pregnadiene-11β, 21-diol-3,6,20-trione 21-acetate of formula III, the therapeutic topical dosages will generally be lower than those required when administering the corresponding 6-unsubstituted-1,4-pregnadiene analogs. The various topical forms and their mode of administration in which the preferred 6-oxo-1,4-pregnadienes are most useful are similar to those described hereinabove for the preferred 6-acyloxy-1,4,6-pregnatrienes of formula II.

Also within the scope of my invention are pharmaceutical compositions for use in the treatment of inflammation comprising an effective amount of our novel 3,20-dioxo-6-acyloxy-1,4,6-pregnatrienes and 4,6-pregnadienes of formula I or of our novel 3,6,20-trioxo-1,4-pregnadienes of formula III in association with a compatible, pharmaceutically acceptable carrier or coating. Of the foregoing, one preferred group includes pharmaceutical compositions for topical administration comprising the 16-methyl-3,20-dioxo-1,4,6-pregnatrienes of formula II of which the 6,17,21-triesters, particularly those having a 17 or 21-propionate group, are of greatest value as topical anti-inflammatories. Another preferred group includes pharmaceutical compositions for topical administration comprising the 3,6,20-trioxo-16-methyl-1,4-pregnadienes of formula IV, particularly those having a 17-propionate group, which possess high topical activity generally superior to the 6-unsubstituted analogs and to the corresponding 6-acyloxy-6,7-dihydro derivatives.

The pharmaceutical dosage forms are prepared according to procedures well known in the art and may contain other active ingredients, e.g., neomycin sulfate in cream for topical use.

The active steroid may be formulated into a preparation suitable for topical administration in conventional manner with the aid of one or more carriers or excipients. Examples of types of preparation include ointments, lotions, creams, sprays, powders, drops (e.g., ear drops and eye drops), suppositories or retention enemas (e.g., for the treatment of rectal or colonic inflammations) and tablets or pellets (e.g., for the treatment of aphthous ulcers) and aerosols. Ointments and creams may, for example, be formulated with an aqueous or oily base with the addition of suitable thickening and/or gelling agents. Such bases may thus, for example, include water and/or an oil such as liquid paraffin or a vegetable oil such as peanut oil or castor oil. Thickening agents which may be used according to the nature of the base include soft paraffin, aluminum stearate, cetostearyl alcohols, polyethylene glycols, woolfat, hydrogenated lanolin, beeswax, etc.

Lotions may be formulated with an aqueous or oily base and will in general also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The pharmaceutical compositions according to the invention may also include one or more preservatives or bacteriostatic agents, e.g., methyl hydroxybenzoate, propyl hydroxybenzoate, chlorocresol, benzalkonium chlorides, etc.

The compositions according to the invention may also contain other active ingredients such as antimicrobial agents, particularly antiobiotics.

The proportion of active steroid in the compositions according to the invention depends on the precise type of formulations to be prepared but will generally be within the range of from 0.0001% to 5% by weight. Generally, however, for most types of preparations advantageously the proportion used will be within the range of from 0.001 to 0.5% and preferably 0.01to 0.25%.

The following illustrate topical formulations prepared in accordance with our invention. In each, the active ingredient is 9α-fluoro-16β-methyl1,4-pregnadiene-6,11β, 17α, 21-tetrol-3,20-dione 6,17,21-tripropionate. It will be appreciated, however, that this compound may be replaced by equivalent quantities of other active 6-acyloxy compounds of this invention, e.g., by the 6,21-dipropionate 17-isobutyrate or the 6-acetate 17,21- dipropionate of 9α-fluoro-16β-methyl-1,4,6-pregnatriene-6,11β,17α,21-tetrol-3,20-dione or by equivalent quantities of active 3,6,20-trioxo-1,4-pregnadienes of the invention, e.g., by 9α-fluoro-16β-methyl-1,4-pregnadiene-11β,17α, 21-triol-3,6,20-trione 17,21-dipropionate, 9α-fluoro-16α-methyl-1,4-pregnadiene-11β,17α,21-triol-3,6,20-trione 17-isobutyrate, or by 9α-fluoro-16α,17β-isopropylidenedioxy-1,4-pregnadiene-11β,21-diol-3,6,20-trione 21-acetate.

FORMULATIONS

1. Ointment

|  | mg/g |
| --- | --- |
| 9α-fluoro-16β-methyl-1,4,6-pregnatriene-6,11β,17α,21-tetrol-3,20-dione 6,17,21-tripropionate, Micronized | 0.1–5.0 |
| Mineral Oil | 20.0 |
| White Petrolatum to make | 1.00 g |

Melt and heat the white petrolatum to 55° C. Heat the mineral oil to 40° C. Disperse the 9α-fluoro-16β-methyl-1,4,6-pregnatriene-6,11β,17α,21-tetrol-3,20-dione 6,17,21-tripropionate in the mineral oil and mill the suspension. Add the suspension to the melted white petrolatum with agitation. Start cooling and continue to agitate until the temperature reaches 30° C.

2. Glycol Ointment

|  | mg/g |
| --- | --- |
| 9α-fluoro-16β-methyl-1,4,6-pregnatriene-6,11β,17α,21-tetrol-5,20-dione 6,17,21-tripropionate | 0.1–0.5 |
| Hexylene Glycol | 100.0 |
| Propylene Glycol Monostearate | 20.0 |
| White wax | 60.0 |
| White petrolatum to make | 1.00 g |

Melt and heat together to 60°–65° C. the propylene glycol monostearate, white wax and white petrolatum. Heat the hexylene glycol to 40° C. and dissolve the 9α-fluoro-16β-methyl-1,4,6-pregnatriene-6,11β,17α,21-tetrol-3,20-dione 6,17,21-tripropionate in it. Add the solution of the hexylene glycol to the above oily phase (cooled to 55° C.) with agitation. Start cooling and continue to agitate until the temperature reaches 30° C.

3. Lotion

|  | mg/g |
| --- | --- |
| 9α-fluoro-16β-methyl-1,4,6-pregnatriene-6,11β,17α,21-tetrol-3,20-dione 6,17,21-tripropionate | 0.1–5.0 |
| Ethyl Alcohol | 400.0 |
| Polyethylene Glycol 400 | 300.0 |
| Hydroxypropyl Cellulose | 5.0 |
| Propylene Glycol to make | 1.0 g |

Dissolve the 9α-fluoro-16β-methyl-1,4,6-pregnatriene-6,11β,17α,21-tetrol-3,20-dione 6,17,21-tripropionate in the mixture of the ethyl alcohol polyethylene glycol and propylene glycol. Slowly add the hydroxypropyl cellulose and continue to agitate until the hydroxypropyl cellulose is completely dispersed and wetted and a clear lotion is produced.

4. Gel

|  | mg/g |
| --- | --- |
| 9α-fluoro-16β-methyl-1,4,6-pregnatriene-6,11β,17α,21-tetrol-3,20-dione 6,17,21-tripropionate | 0.1–5.0 |
| Ethyl Alcohol | 400.0 |
| Polyethylene Glycol 400 | 300.0 |
| Carbopol 940 (Goodrich) | 15.0 |
| Potassium Hydroxide | 3.0 |
| Propylene Glycol to make | 1.00 g |

Dissolve the 9α-fluoro-16β-methyl-1,4,6-pregnatriene-6,11β,17α,21-tetrol-3,20-dione 6,17,21-tripropionate in a mixture of the ethyl alcohol, polyethylene glycol 400 and a portion of the propylene glycol. Use the remaining portion of the propylene glycol to dissolve the potassium hydroxide. Add the Carbopol 940 slowly to the above mixture and continue to agitate until the Carbopol 940 is completely dispersed and wetted. Add slowly the potassium hydroxide solution and continue to agitate until a clear gel is produced.

5. Cream

|  | mg/g |
| --- | --- |
| 9α-fluoro-16β-methyl-1,4,6-pregnatriene-6,11β,17α,21-tetrol-3,20-dione 6,17,21-tripropionate, Micronized | 0.1–5.0 |
| Isopropyl Palmitate | 100.0 |
| Glyceryl Stearate | 80.0 |
| Promulgen-Type D (Robinson, Wagrer Co.) | 50.0 |
| White wax | 50.0 |
| Propylene Glycol | 100.0 |
| Purified water to make | 1.00 g |

Melt together and heat to 75° C. the white wax, glyceryl stearate, Promulgen-Type D and a portion of the isopropyl palmitate and maintain the temperature. Disperse the 9α-fluoro-16β-methyl-1,4,6-pregnatriene-6,11β,17α,21-tetrol-3,20-dione 6,17,21-tripropionate in the remaining portion of the isopropyl palmitate and mill the dispersion. While agitating add the dispersion to the above oily phase. Heat together the water and the propylene glycol to 75° C. Add the solution to the above oily phase with agitation. Start cooling and continue to agitate until the temperature reaches 30° C.

6. Topical Aerosol

|  | mg/can |
| --- | --- |
| 9α-fluoro-16β-methyl-1,4,6-pregnatriene-6,11β,17α,21-tetral-5,20-dione 6,17,21-tripropionate | 6.4 |
| Mineral Oil | 1,250.0 |
| Neobee M-5 (Caprylic/Capric Glyceride) (PVO International, Inc.) | 3,743.6 |
| Dichlorodifluoromethane | 17,200.0 |
| Trichloromonofluoromethane | 68,800.0 |
|  | 91,000.0 |

Dissolve the 9α-fluoro-16β-methyl-1,4,6-pregnatriene-6,11β,17α,21-tetrol-3,20-dione 6,17,21-tripropionate in Neobee M-5 (Caprylic/Capric Glyceride) and add mineral oil. Place this concentrate into an aerosol and crimp a valve on the can. Inject the dichlorodifluoromethane and trichloromonofluoromethane mixture into the container through the valve.

7. Inhalation Aerosol

|  | mg/can |
|---|---|
| 9α-fluoro-16β-methyl-1,4,6-pregna-triene-6,11β,17α,21-tetrol-3,20-dione 6,17,21-tripropionate | 12.60 |
| Oleic Acid | 1.26 |
| Trichloromonofluoromethane | 5,686.14 |
| Dichlorodifluoromethane | 14,700.00 |
|  | 20,400.00 |

Disperse the 9α-fluoro-16β-methyl-1,4,6-pregnatriene-6,11β,17α,21-tetrol-3,20-dione 6,17,21-tripropionate in trichloromonofluoromethane containing oleic acid and meter the resulting suspension into the cans. Crimp a valve onto the can and inject dichlorodifluoromethane into the container through the valve.

8. Intra-Articular Injection

|  | mg/ml |
|---|---|
| 9α-fluoro-16β-methyl-1,4,6-pregna-triene-6,11β,17α,21-tetrol-3,20-dione 6,17,21-tripropionate | 0.1–5.0 |
| Sodium Phosphate, dibasic, anhydrous R | 2.00 |
| Sodium Chloride, USP | 5.00 |
| Disodium EDTA, USP (Disodium Ethylenediamine tetraacetate) | 0.10 |
| Polysorbate 80, USP | 0.50 |
| Benzyl Alcohol, R | 9.00 |
| Methylparaben, USP | 1.80 |
| Propylparaben, USP | 0.20 |
| Sodium CMC (Sodium carboxymethylcellulose) | 5.00 |
| Polyethylene Glycol 4000, USP | 20.00 |
| HCl 1N qs pH 7.1 |  |
| Distilled water qs ad | 1.00 ml |

Method of Manufacture:

| Vehicle A (10X) | mg/ml | gm/5 liters (required to make 50 liters final suspension) |
|---|---|---|
| Sodium phosphate, Dibasic, Anhydrous, R | 20.0 | 100.0 |
| Sodium Chloride, R | 50.0 | 250.0 |
| Disodium EDTA, Dihydrate, R | 1.0 | 5.0 |
| Polysorbate 80, USP | 5.0 | 25.0 |
| 1N HCl qs pH 7.10 |  |  |
| Water for Injection qs ad | 1.0 ml | 5.0 liters |

1. Collect approximately 80% of water for injection of the final volume of Vehicle A. Sparge with nitrogen.
2. Dissolve with agitation the Disodium EDTA, dibasic sodium phosphate, sodium chloride. Discontinue nitrogen sparging and disperse the Polysorbate 80 while overlaying with nitrogen.
3. Adjust the pH of the solution to 7.1 with 1.0 N hydrochloric acid solution, then add sufficient water to bring Vehicle A to the required volume. Sterile filter, overlay with sterile nitrogen.

| Vehicle B (1.33X) | mg/ml | gm/37.5 liters (required to make 50 liters final suspension) |
|---|---|---|
| Benzyl Alcohol, R | 12.000 | 450.0 |
| Methylparaben, USP | 2.400 | 90.0 |
| Propylparaben, USP | 0.266 | 10.0 |
| Sodium Carboxymethylcellulose | 6.670 | 250.0 |
| Polyethlene Glycol 4000, USP | 26.670 | 1,000.0 |
| Water for Injection, qs ad | 1.000 ml | 37.5 liters |

1. Charge approximately 95% (35.6 liters) of the water for injection.
2. Separately dissolve the methyl and propylparaben in the benzyl alcohol, then add the sodium carboxymethylcellulose and add this slurry to the water for injection.
3. Charge the polyethylene glycol 4000, USP.
4. Bring the volume of Vehicle B to the final volume and pass through an 8.0μ Millipore membrane into containers for autoclaving.

| Final Suspension | per liter | per 50 liters |
|---|---|---|
| 9α-fluoro-16β-methyl-1,4,6-pregna-triene-6,11β,17α,21-tetrol-3,20-dione 6,17,21-tripropionate | 0.1 to 5.0 gm | 5.0 to 250 gm |
| Vehicle A | 100.00 ml | 5,000.0 ml |
| Vehicle B | 750.00 ml | 37,500.0 ml |
| Water for Injection qs ad | 1,000.00 ml | 50.0 liters |

1. In a suitable sterile area, charge 27.5 liters of Vehicle B to a compounding tank.
2. Disperse the steroid in a minimum quantity of Vehicle A, and pass the slurry through a colloid mill until the particles are well dispersed, then rinse the mill with the remainder of Vehicle A.
3. Add to the slurry an approximate equal volume of Vehicle B, pass the resultant flocculated suspension through the mill, then pass the suspension through a sterile mesh screen into the compounding tank.
4. Rinse the mill with part of Vehicle B followed by water, pass the rinse through the screen into the compounding tank. Add the remainder of Vehicle B, then water, to bring the batch up to the required volume. Mix well.
5. Fill aseptically into siliconed vials and/or ampules, overlay with nitrogen, and stopper.

9. Solution

| Solution | mg/ml |
|---|---|
| 9α-fluoro-16β-methyl-1,4,6-pregna-triene-6,11β,17α,21-tetrol-3,20-dione 6,17,21-tripropionate | 0.1–5.0 |
| N-methylpyrrolidone | 200 |
| Isopropyl myristate | 50 |
| Isopropyl alcohol | qs to 1.0 ml |

Dissolve the 9α-fluoro-16β-methyl-1,4,6-pregnatriene-6,11β,17α,21-tetrol-3,20-dione 6,17,21-tripropionate in a portion of the N-methylpyrrolidone. Mix the isopropyl myristate with a portion of isopropyl alcohol. Mix the two solutions, add the remainder of the N-methylpyrrolidone, then isopropyl alcohol to the desired volume.

The processes described hereinabove are illustrated in detail in the Examples hereinbelow and should not be construed as limiting the invention, equivalents thereof and products produced thereby which will be obvious to one skilled in the art being considered a part of the invention.

The molecular structure of the compounds of the invention described in detail hereinbelow were assigned on the basis of their method of preparation and study of their chromatographic characteristics and of the their nuclear magnetic resonance (nmr), mass spectra and ultraviolet spectra, and were confirmed by the correspondence between calculated and found values of elementary analyses for the elements.

PREPARATION 1

9α-FLUORO-16-METHYL-1,4-PREGNADIENE-6β,11β,17α,21-TETROL-3,20-DIONE 21-ACETATES

A.

9α-Fluoro-16β-Methyl-1,4-Pregnadiene-6β,11β,17α,21-Tetrol-3,20-Dione 21-Acetate (1) To a solution of 9α-fluoro-16β-methyl-1,4-pregnadiene-11β,17α,21-triol-3,20-dione 21-acetate (20 gms.) in dry pyridine (160 ml.) add benzoyl chloride (80 ml.) and heat the reaction mixture under an atmosphere of nitrogen at 62° C. for 18 hours. Cool and pour the reaction mixture onto ice cold dilute hydrochloric acid, and extract with ethyl acetate. Wash the combined ethyl acetate extracts with water and evaporate. Chromatograph the resultant residue over silica gel eluting first with petroleum ether:ether (4:1) to remove benzoyl chloride, then eluting with ether. Evaporate the combined ether eluates to a residue comprising 9α-fluoro-16β-methyl-1,3,5-pregnatriene-3,11β,17α,21-tetrol-20-one 3-benzoate 21-acetate.

(2) Without further purification, dissolve the foregoing pregnatriene 3-benzoate 21-acetate product in chloroform (250 ml.) and bubble oxygen into the solution for 5 hours. Separate the resultant precipitate by filtration and dry to obtain 9α-fluoro-16β-methyl-1,4-pregnadiene-6β,11β,17α,21-tetrol-3,20-dione 21-acetate (yield=10.6 gms.), m.p. 195°–196° C.; $[\alpha]_D^{26}$ +68° (pyridine) $\lambda_{max}$ 240 nm ($\epsilon$=16,800).

B.

9α-Fluoro-16α-Methyl-1,4-Pregnadiene-6β,11β,17α,21-Tetrol-3,20-Dione 21-Acetate

In the procedure of Preparation 1A, utilize as starting compound 9α-fluoro-16α-methyl-1,4-pregnadiene-11β,17α,21-triol-3,20-dione 21-acetate to obtain 9α-fluoro-16α-methyl-1,4-pregnadiene-6β,11β,17α,21-tetrol-3,20-dione 21-acetate, m.p. 200°–204° C.; $[\alpha]_D^{26}$ +48.0° (pyridine); $\lambda_{max}^{methanol}$ 238 nm ($\epsilon$=15,400).

PREPARATION 2

9α,11β-DICHLORO-16α-METHYL-1,4-PREGNADIENE-6β,17α,21-TRIOL-3,20-DIONE 21-ACETATE (1) To a solution of 9α,11β-dichloro-16α-methyl-1,4-pregnadiene-17α,21-diol-3,20-dione 21-acetate (5 gms.) in pyridine (40 ml.) add benzoyl chloride (20 ml.) and stir at 70° C. under an atmosphere of nitrogen overnight. Cool the reaction mixture and pour into cold dilute hydrochloric acid. Extract with ether, wash the combined extracts with water, dry over magnesium sulfate, then evaporate and chromatograph the resultant residue over silica gel eluting with petroleum ether:ether gradient. Monitor the eluates via thin layer chromatography and combine the latter like eluates and evaporate to a residue comprising 9α,11β-dichloro-16α-methyl-1,3,5-pregnatriene-3,17α,21-triol-20-one 3-benzoate 21-acetate. Purify by crystallization from ether (yield 2.78 gms.).

(2) Without further purification, dissolve the foregoing pregnatriene 3-benzoate 21-acetate in chloroform (75 ml.) and bubble oxygen through the solution for 5 hours. Evaporate the reaction mixture and chromatograph the resultant residue over silica gel eluting with chloroform:ether acetate (7:3). Combine the like eluates as determined by thin layer chromatography and evaporate to a residue comprising 9α,11β-dichloro-16α-methyl-1,4-pregnadiene-6β,17α,21-triol-3,20-dione 21-acetate. Purify by crystallization from ether, m.p. 210°–212° C.; $[\alpha]_D^{26}$+87° (chloroform); $\lambda_{max}$ 238 nm ($\epsilon$=15,600).

PREPARATION 3

9α-HALOGENO-16β-METHYL-1,4-PREGNADIENE-6β,11β,17α,21-TETROL-3,20-DIONE 17,21-DIPROPIONATES

A.

9α-Chloro-16β-Methyl-1,4-Pregnadiene-6β,11β,17α,21-Tetrol-3,20-Dione 17,21-Dipropionate In a manner similar to that described in Preparation 1A, treat a solution of 9α-chloro-16β-methyl-1,4-pregnadiene-11β,17α,21-triol-3,20-dione 17,21-dipropionate (10 gms.) in pyridine (80 ml.) containing benzoyl chloride (20 ml.) at 65° C. under an atmosphere of nitrogen, then isolate the resultant product in a manner similar to that described. Purify by chromatographing over silica gel eluting first with methylene chloride to remove the excess benzoyl chloride, then eluting with ethyl acetate and evaporating the ethyl acetate eluates to a residue comprising 9α-chloro-16β-methyl-1,3,5-pregnatriene-3,11β,17α,21-tetrol-20-one 3-benzoate 17,21-dipropionate. Without further purification, dissolve the foregoing pregnatriene 3-benzoate 17,21-dipropionate product is chloroform (250 ml.), bubble oxygen through the solution for 5 hours, concentrate and chromatograph the resultant residue over silica gel eluting with methylene chloride:ethyl acetate (4:1). Combine the like fractions as determined by thin layer chromatography and evaporate the combined fractions to a residue comprising 9α-chloro-16β-methyl-1,4-pregnadiene-6β,11β,17α,21-tetrol-3,20-dione 17,21-dipropionate. Purify by crystallization from acetone-hexane (yield 1.8 gms.), m.p. 253°–258° C.; $[\alpha]_D^{26}$+Δ9°(dioxane), $\lambda_{max}$ 238 nm ($\epsilon$=16,000).

B.

9α-Fluro-16β-Methyl-1,4-Pregnadiene-6β,11β,17α,21-Tetrol-3,20-Dione 17,21-Dipropionate In the above precedure, utilize as starting compound 9α-fluoro-16β-methyl-1,4-pregnadiene-11β,17α,21-triol-3,20-dione 17,21-dipropionate to obtain 9α-fluoro-16β-methyl-1,4-pregnadiene-6,11β,17α,21-tetrol-3,20-dione 17,21-dipropionate; $[\alpha]_D^{26}$+300 (CHCl$_3$); $\lambda_{max}$ 240 nm ($\epsilon$=16,500).

PREPARATION 4

9α-FLUORO-16α,17α-ISOPROPYLIDENEDIOXY-1,4-PREGNADIENE-6β,11β,21-TRIOL-3,20-DIONE 21-ACETATE (1) In a manner similar to that described in the first paragraph of Preparation 1A, treat a solution of 9α-fluoro-16α,17α-isopropylidenedioxy-1,4-pregnadiene-11β,21-diol-3,20-dione 21-acetate (10 gms.) in pyridine (80 ml.) in the presence of benzoyl chloride (20 ml.) under an atmosphere of nitrogen at 65° C. overnight. Isolate the resultant product in the described manner to obtain 9α-fluoro-16α,17α-isopropylidenedioxy-1,3,5-pregnatriene-3,11β,21-triol-20-one 3-benzoate 21-acetate.

(2) Treat the foregoing 1,3,5-pregnatriene 3-benzoate 21-acetate in chloroform with oxygen in a manner similar to that described in the second paragraph of Preparation 1A, and isolate the resultant product in a manner similar to that described to obtain 9α-fluoro-16α,17α-isopropylidenedioxy-1,4-pregnadiene-6β,11β,21-triol-3,20-dione 21-acetate; m.p. 290°–294° C., $[\alpha]_D^{26}+53°$ (dioxane), $\lambda_{max}$ 237 nm ($\epsilon=14,500$).

EXAMPLE 1

9α-FLUORO-16-METHYL-1,4-PREGNADIENE-11β,17α,21-TRIOL-3,6,20-TRIONE 21-ACETATES

A.

9α-Fluoro-16β-Methyl-1,4-Pregnadiene-11β,17α,21-Triol-3,6,20-Trione 21-Acetate Stir overnight at room temperature a mixture of 9α-fluoro-16β-methyl-1,4-pregnadiene-6β,11β,17α,21-tetrol-3,20-dione 21-acetate (460 mg., 1 mmol) N,N-dicyclohexylcarbodiimide (617 mg., 3 mmol), pyridine (0.08 ml., 1 mmol), trifluoroacetic acid (0.04 ml., 1 mmol), in benzene (3.3 ml.) and dimethylsulfoxide (1.7 ml.). Dilute the reaction mixture with ethyl acetate, separate the solids by filtration and wash with ethyl acetate. Combine the ethyl acetate filtrate and washings, wash with water, and evaporate. Chromatograph the resultant residue over silica gel eluting with a petroluem ether:ether gradient. Combine the like eluates containing the desired product as determined by thin layer chromatography and evaporate to a residue comprising 9α-fluoro-16β-methyl-1,4-pregnadiene-11β, 17α,21-triol-3,6,20-trione 21-acetate. Purify by crystallization from ether; m.p. 200°–202° C., $[\alpha]_D^{26}-7°$ (chloroform), λ max 250 nm ($\epsilon=14,200$).

B.

9α-Fluoro-16α-Methyl-1,4-Pregnadiene-11β,17α,21-Triol-3,6,20-Trione 21-Acetate In the procedure of Example 1A, by starting with 9α-fluoro-16α-methyl-1,4-pregnadiene-6β,11β,17α,21-tetrol-3,20-dione 21-acetate, there is obtained 9α-fluoro-16α-methyl-1,4-pregnadiene-11β,17α,21-triol-3,6,20-trione 21-acetate, m.p. 260° C.; $[\alpha]_D^{26}-17°$ (chloroform); λ max 247 ($\epsilon=14,500$).

EXAMPLE 2

9α,11β-DICHLORO-16α-METHYL-1,4-PREGNADIENE-17α,21-DIOL-3,6,20-TRIONE 21-ACETATE

In a manner similar to that described in Example 1A, treat 9α,11β-dichloro-16α-methyl-1,4-pregnadiene-6β,17α,21-triol-3,20-dione 21-acetate with N,N-dicyclohexylcarbodiimide in dimethylsulfoxide and benzene in the presence of pyridine and trifluoroacetic acid at room temperature for 3 hours. Isolate and chromatograph the resultant product in a manner similar to that described to obtain 9α,11β-dichloro-16α-methyl-1,4-pregnadiene-17α,21-diol-3,6,20-trione 21-acetate. Purify by crystallization from chloroform:ethyl acetate, m.p. 227°–228° C., $[\alpha]_D^{26}+22°$ (chloroform), λ max 247 nm ($\epsilon=11,600$).

EXAMPLE 3

9α-HALOGENO-16β-METHYL-1,4-PREGNADIENE-11β,17α,21-TRIOL-3,6,20-TRIONE 17,21-DIPROPIONATES

A.

9α-Chloro-16β-Methyl-1,4-Pregnadiene-11β,17α,21-Triol-3,6,20-Dione 17,21-Dipropionate Stir at room temperature for 2 hours a mixture of 9α-chloro-16β-methyl-1,4-pregnadiene-6β,11β,17α,21-tetrol-3,20-dione 17,21-dipropionate (1.611 gms., 3 mmol), 1-cyclohexyl-3-(2-morpholinoethyl)-carbodiimide metho-p-toluenesulfonate (3.81 gms., 9 mmol), pyridine (0.24 ml., 3 mmol) and trifluoroacetic acid (0.12 ml., 1.5 mmol) in benzene (10 ml.) and dimethylsulfoxide (5 ml.). Dilute the reaction mixture with ethyl acetate (150 ml.), separate the solids by filtration and wash with ethyl acetate. Combine the ethyl acetate filtrate and washings, wash with dilute hydrochloric acid, then with water, dry over magnesium sulfate and evaporate in vacuo. Crystallize the resultant residue from ethyl acetate to obtain 9α-chloro-16β-methyl-1,4-pregnadiene-11β,17α,21-triol-3,6,20-trione 17,21-dipropionate, m.p. 235°–236° C., $[\alpha]_D^{26}-14°$ (chloroform), λ max 249 nm ($\epsilon=13,700$).

B.

9α-Fluoro-16β-Methyl-1,4-Pregnadiene-11β,17α,21-Triol-3,6,20-Trione 17,21-Dipropionate In the procedure of Example 3A, by utilizing as starting compound 9α-fluoro-16β-methyl-1,4-pregnadiene-6β,11β,17α,21-tetrol-3,20-dione 17,21-dipropionate, there is obtained 9α-fluoro-16β-methyl-1,4-pregnadiene-11β,17α,21-triol-3,6,20-trione 17,21-dipropionate, m.p. 188°–190° C. $[\alpha]_D^{26}-29°$ (chloroform), λ max 247 nm ($\epsilon=13,600$).

EXAMPLE 4

9α-FLUORO-16α,17α-ISOPROPYLIDENEDIOXY-1,4-PREGNADIENE-11β, 21-DIOL-3,6,20-TRIONE 21-ACETATE

In a manner similar to that described in Example 3A, treat 9α-fluoro-16α,17α-isopropylidenedioxy-1,4-pregnadiene-6β,11β,21-triol-3,20-dione 21-acetate with 1-cyclohexyl-3-(2-morpholinoethyl)-carbodiimide metho-p-toluenesulfonate in dimethylsulfoxide and benzene in the presence of pyridine and trifluoroacetic acid, and isolate and purify the resultant product in the described manner to obtain 9α-fluoro-16α,17α-isopropylidenedioxy-1,4-pregnadiene-11β,21-diol-3,6,20-trione 21-acetate, m.p. 280°–282° C., $[\alpha]_D^{26}-7°$ (chloroform), λ max 247 nm ($\epsilon=14,000$).

EXAMPLE 5

9α-HALOGENO-16-METHYL-1,4-PREGNADIENE-17α,21-DIOL-3,6,20-TRIONES

A.

9α-Fluoro-16β-Methyl-1,4-Pregnadiene-11β,17α,21-Triol-3,6,20-Trione

To a solution of 9α-fluoro-16β-methyl-1,4-pregnadiene-11β,17α,21-triol-3,6,20-trione 21-acetate (2 gms.) in methanol (100 ml.) add aqueous sodium bicarbonate (40 ml., 10%), and stir the mixture at room temperature overnight. Evaporate in vacuo and partition the resultant residue between water and ethyl acetate. Wash the ethyl acetate layer with water, dry over magnesium sulfate, concentrate to a small volume and allow to crystallize. Filter the resultant crystals and dry to obtain 9α-fluoro-16β-methyl-1,4-pregnadiene-11β,17α,21-triol-3,6,20-trione, m.p., 239°–242° C., $[\alpha]_D \approx -2°$ (chloroform), λ max 238 nm (ε=13,500).

B. Treat each of 9α-fluoro-16α-methyl-1,4-pregnadiene-11β,17α,21-triol-3,6,20-trione 21-acetate and 9α,11β-dichloro-16α-methyl-1,4-pregnadiene-17α,21-diol-3,6,20-trione 21-acetate with aqueous sodium bicarbonate in the manner of Example 5A, and isolate and purify each of the resultant products in a manner similar to that described to obtain 9α-fluoro-16α-methyl-1,4-pregnadiene-11β,17α,21-triol-3,6,20-trione and 9α,11β-dichloro-16α-methyl-1,4-pregnadiene-17α,21-diol-3,6,20-trione, respectively.

EXAMPLE 6

9α-HALOGENO-1,4-PREGNADIENE-11β,17α,21-TRIOL-3,6,20-TRIONE 17-LOWER ALKANOATES

A.

9α-Fluoro-16β-Methyl-1,4-Pregnadiene-11β,17α,21-Triol-3,6,20-Trione 17-Isobutyrate (1) Stir at room temperature for 18 hours a mixture of 9α-fluoro-16β-methyl-1,4-pregnadiene-11β, 17α,21-triol-3,6,20-trione (500 mg.) in dimethylsulfoxide (7 ml.) and triethylorthoisobutyrate (0.7 ml.) and p-toluenesulfonic acid (70 mg.).

(2) To the reaction mixture containing 9α-fluoro-16β-methyl-1,4-pregnadiene-11β,17α,21-triol-3,6,20-trione 17,21-ethylorthoisobutyrate add acetic acid (5 ml.) and water (0.5 ml.) and stir at room temperature for 18 hours. Dilute the reaction mixture with water, extract with ether, wash the combined ether extracts with aqueous sodium bicarbonate, then dry over magnesium sulfate and evaporate. Crystallize the resultant residue from methylene chloride:ether to obtain 9α-fluoro-16β-methyl-1,4-pregnadiene-11β,17α,21-triol-3,6,20-trione 17-isobutyrate, m.p. 214°–217° C., $[\alpha]_D^{26} -29°$ (chloroform), λ max 248 nm (ε=13,800).

B. 9α-Fluoro-16β-Methyl-1,4-Pregnadiene-11β,17α,21-Triol-3,6,20-Trione 17-Lower Alkanoates In a manner similar to that described in Example 6A, treat 9α-fluoro-16β-methyl-1,4-pregnadiene-11β,17α,21-triol -3,6,20-trione with each of the following trialkylorthoesters, followed by reaction of the resulting 17,21-alkylorthoester with dilute acetic acid.

(1) triethylorthopropionate,
(2) triethylortho-n-butyrate,
(3) tri-n-butylorthovalerate,
(4) trimethylorthobenzoate.

Isolate and purify each of the resultant products in a manner similar to that described to obtain, respectively, (1) 9α-fluoro-16β-methyl-1,4-pregnadiene-11β,17α,21-triol-3,6,20-trione 17-propionate,
(2) 9α-fluoro-16β-methyl-1,4-pregnadiene-11β,17α,21-triol-3,6,20-trione 17-n-butyrate,
(3) 9α-fluoro-16β-methyl-1,4-pregnadiene-11β,17α,21-triol-3,6,20-trione 17-valerate,
(4) 9α-fluoro-16β-methyl-1,4-pregnadiene-11β,17α,21-triol-3,6,20-trione 17-benzoate.

C. In a manner similar to that described in Example 6B, treat 9α-fluoro-16α-methyl-1,4-pregnadiene-11β,17α,21-triol-3,6,20-trione with each of
(1) triethylorthopropionate,
(2) triethylorthoisobutyrate,
(3) tri-n-butylorthovalerate,
followed by treatment of the resulting 17,21-alkylorthoester with dilute acetic acid. Isolate and purify each of the resulting products in a manner similar to that described in Example 6B to obtain, respectively, (1) 9α-fluoro-16α-methyl-1,4-pregnadiene-11β,17α,21-triol-3,6,20-trione 17-propionate,
(2) 9α-fluoro-16α-methyl-1,4-pregnadiene-11β,17α,21-triol-3,6,20-trione 17-isobutyrate,
(3) 9α-fluoro-16α-methyl-1,4-pregnadiene-11β, 17α, 21-triol-3,6,20-trione 17-valerate.

D. In a manner similar to that described in Example 6A, treat 9α,11β-dichloro-16α-methyl-1,4-pregnadiene-17α,21-diol-3,6,20-trione with triethylorthopropionate followed by treatment of the resulting 17,21-orthoester with dilute acetic acid. Isolate and purify the resulting product in a manner similar to that described to obtain 9α,11β-dichloro-16α-methyl-1,4-pregnadiene-17,21-diol-3,6,20-trione 17-propionate.

EXAMPLE 7

9α-FLUORO-16β-METHYL-1,4-PREGNADIENE-11β,17α,21-TRIOL-3,6,20-TRIONE 21-TRIMETHYLACETATE

Prepare a solution of 9α-fluoro-16β-methyl-1,4-pregnadiene-11β,17α,21-triol-3,6,20-trione (200 mg.) in pyridine (3 ml.) containing trimethylacetic anhydride (1 ml.) and keep at room temperature for 72 hours. Pour the reaction mixture into dilute hydrochloric acid and extract with ether. Wash the combined ether extracts with water and dry over magnesium sulfate. Evaporate the combined extracts to a residue comprising 9α-fluoro-16β-methyl-1,4-pregnadiene-11β,17α,21-triol-3,6,20-trione 21-trimethylacetate. Purify the residue by chromatographing over silica gel with gradient elution with petroleum ether/ether. Combine the like eluates of desired product as determined by thin layer chromatography and evaporate the combined eluates to a residue followed by crystallization of the residue from ether to obtain 9α-fluoro-16β-methyl-1,4-pregnadiene-11β,17α,21-triol-3,6,20-trione 21-trimethylacetate; yield 140 mg., m.p. 153°–155° C., λ max 250 nm (ε=13,800).

In similar manner treat each of 9α-fluoro-16α-methyl-1,4-pregnadiene-11β,17α,21-triol-3,6,20-trione and 9α,11β-dichloro-16α-methyl-1,4-pregnadiene-17α,21-diol-3,6,20-trione with trimethylacetic anhydride in pyridine followed by isolation and purification in a manner similar to that described to obtain, respectively, 9α-fluoro-16α-methyl-1,4-pregnadiene-11β,17α,21-triol-3,6,20-trione 21-trimethylacetate and 9α,11β-dichloro-16α-methyl-1,4-pregnadiene-17α,21-diol-3,6,20-trione 21-trimethylacetate.

EXAMPLE 8

1,4-PREGNADIENE-17α,21-DIOL-3,6,11,20-TETRONES

A.

9α-Fluoro-16β-Methyl-1,4-Pregnadiene-17α,21-Diol-3,6,11,20-Tetrone 21-Acetate

To a solution of 9α-fluoro-16β-methyl-1,4-pregnadiene-6β, 11β,17α,21-tetrol-3,20-dione 21-acetate (1 gm.) in acetone (50 ml.) with stirring add a Kiliani chromic acid (1 ml.) (Fieser and Fieser Reagents for Organic Synthesis, Vol. 1, page 144, 1967, John Wiley and Sons, Inc.). Allow to stand at room teperature for 4 hours with occasional stirring. Dilute the mixture with water (100 ml.) and extract with ethyl acetate. Wash the combined ethyl acetate extracts with water, dry over magnesium sulfate and evaporate in vacuo. Crystallize the resultant residue from methylene chloride/ether to obtain 9α-fluoro-16β-methyl-1,4-pregnadiene-17α,21-diol-3,6,11,20-tetrone 21-acetate, yield 563 mg., m.p. 222°-225° C., $[\alpha]_D^{26}$ +57° (chloroform), λ max 242 nm (ε=14,300).

(2) In the procedure of above Example 8A, by utilizing as starting compound 9α-fluoro-16β-methyl-1,4-pregnadiene-11β, 17α,21-triol-3,6,20-trione 21-acetate, there is obtained the corresponding 6,11-dioxo derivative of this example.

B. In similar manner, treat each of the 11β-hydroxy compounds prepared in Examples 1B, 3, 4 and 7 with a Kiliani chromic acid reagent to obtain the corresponding 11-oxo derivative, i.e. 9α-fluoro-16α-methyl-1,4-pregnadiene-17α,21-diol-3,6,11,20-tetrone 21-acetate; 9α-chloro-16β-methyl-1,4-pregnadiene-17α,21-diol-3,6,11,20-tetrone 17,21-dipropionate; 9α-fluoro-16β-methyl-1,4-pregnadiene-17α,21-diol-3,6,11,20-tetrone 17,21-dipropionate; 9α-fluoro-16α,17α-isopropylidenedioxy-1,4-pregnadiene-21-ol-3,6,11,20-tetrone 21-acetate; 9α-fluoro-16β-methyl-1,4-pregnadiene-17α,21-diol-3,6,11,20-tetrone 21-trimethylacetate; 9α-fluoro-16α-methyl-1,4-pregnadiene-17α,21-diol-3,6,11,20-tetrone 21-trimethylacetate.

EXAMPLE 9

6-ACYLOXY-9α-HALOGENO-1,4,6-PREGNATRIENE-11β,17α,21-TRIOL-3,20-DIONE 21-ALKANOATES AND 17,21-DIALKANOATES DERIVED FROM THE CORRESPONDING 6-OXO-6,7-DIHYDRO ANALOGS

9α-Fluoro-16β-methyl-1,4,6-Pregnatriene-6,11β,17α,21-Tetrol-3,20-Dione 6-Acetate 17,21-Dipropionate To a solution of 9α-fluoro-16β-methyl-1,4-pregnadiene-11β, 17α,21-triol-3,6,20-trione 17,21-dipropionate (200 mg.) in pyridine (3 ml.) add acetic anhydride (1 ml.) and stir at room temperature for 5 hours. Pour the reaction mixture into dilute hydrochloric acid, separate the resultant precipitate by filtration, wash and air dry. Chromatograph the precipitate over silica gel via gradient elution with petroleum ether containing increasing quantities of ethyl ether. Combine the like eluates containing the desired product as determined by thin layer chromatography, evaporate the combined eluates and recyrstallize the resultant residue from ether to obtain 9α-fluoro-16β-methyl-1,4,6-pregnatriene-6,11β,17α,21-tetrol-3,20-dione 6-acetate 17,21-dipropionate; m.p. 123°-125° C., $[\alpha]_D^{26}$ −12° (chloroform λ $_{max}^{methanol}$ 224 (ε=11,400) 252 (ε=10,100) and 296 nm (ε=10,400), yield=110 mg.

B. Treat the following 6-oxo-1,4-pregnadienes in the manner described in Example 9A:

9α-fluoro-16β-methyl-1,4-pregnadiene-11β,17α,21-triol-3,6,20-trione 21-acetate;
9α-chloro-16β-methyl-1,4-pregnadiene-11β,17α,21-triol-3,6,20-trione 17,21-dipropionate;
9α-fluoro-16α,17α-isopropylidenedioxy-1,4-pregnadiene-11β,21-diol-3,6,20-trione 21-acetate; and
9α-fluoro-16α-methyl-1,4-pregnadiene-11β,17α,21-triol-3,6,20-trione 21-acetate.

Isolate and purify each of the resultant products in a manner similar to that described to obtain, respectively,
9α-fluoro-16β-methyl-1,4,6,-pregnatriene-6,11β,17α,21-tetrol-3,20-dione 6,21-diacetate; m.p. 232°-233° C.; $[\alpha]_D^{26}$ +×° (chloroform); λ $_{max}^{methanol}$ 225 (ε=11,900), 250 (ε=10,100) and 297 nm (ε−11,000);

9α-chloro-16β-methyl-1,4,6-pregnatriene-6,11β,17α,21-tetrol-3,20-dione 6-acetate 17,21-dipropionate; m.p. 125°-130° C. crystallizes; remelts 210°-212° C.; $[\alpha]_D^{26}$ −23° (chloroform); λ $_{max}^{methanol}$ 249 (ε=11,700) and 295 nm (ε=6,500);

9α-fluoro-16α,17α-isopropylidenedioxy-1,4,6-pregnatriene-6,11β,21-triol-3,20-dione 6,21-diacetate; m.p. 268°-270° C. $[\alpha]_D^{26}$ +23° (chloroform) λ $_{max}^{methanol}$ 223 (ε=11,500), 248 (ε=10,300) and 295 nm (ε=10,900); and 9α-fluoro-16α-methyl-1,4,6-pregnatriene-6,11β,17α,21-tetrol-3,20-dione 6,21-diacetate; m.p. 227°-229° C.; $[\alpha]_D^{26}$ +10° (chloroform); λ $_{max}^{methanol}$ 223 (ε=11,600), 250 (ε=10,200), 297 nm (ε=10,300).

C. In the procedure of Example 9A, by substituting propionic anhydride for acetic anhydride, there is obtained the corresponding 6-propionate derivative, i.e. 9α-fluoro-16β-methyl-1,4,6-pregnatriene-6,11β,17α,21 -tetrol-3,20-dione 6,17,21-tripropionate; m.p. 134°-135° C.; $[\alpha]_D^{26}$ −4.8° (chloroform) λ $_{max}^{methanol}$ 225 (ε=11,900), 252 (ε=10,300), 296 nm (ε=11,000).

D. In the procedure of Example 9A, by substituting an equivalent quantity of benzoyl chloride for acetic anhydride, there is obtained the corresponding 6-benzoate ester derivative, i.e., 9α-fluoro-16β-methyl-1,4,6-pregnatriene-6,11β,17α,21-tetrol-3,20-dione 6-benzoate 17,21-dipropionate; $[\alpha]_D^{26}$ +≈° (chloroform); λ $_{max}^{methanol}$ 231 (ε=25,800) and 295 nm (ε=11,000).

EXAMPLE 10

CONVERSION OF 6-OXO-1,4-PREGNADIENE-17-MONOESTERS TO 6-ACYLOXY- 1,4,6-PREGNATRIENE 17,21-DIESTERS

A. 9α-Fluoro-16β-Methyl-1,4,6-Pregnatriene-6,11β,17α,21-Tetrol-3,20-Dione 6,21-Dipropionate 17-Isobutyrate To a solution of 9α-fluoro-16β-methyl-1,4-pregnadiene-11β,17α,21-triol-3,6,20-trione 17-isobutyrate (100 mg.) in pyridine (2 ml.) add propionic ahydride (0.6 ml.) and allow the reaction mixture to stand at room temperature for 5 hours. Pour the reaction mixture into dilute hydrochloric acid, separate the resultant precipitate by filtration, wash, dry and then chromatograph the precipitate over silica gel via gradient elution with petroleum ether containing increasing quantities of ethyl ether. Combine the like fractions containing the desired product as determined by thin layer chromatography, evaporate the combined eluates and recrystallize the resultant residue from ether to obtain 9α-fluoro-16β-methyl-1,4,6-pregnatriene-6,11β,17α,21-tetrol-3,20-dione 6,21-dipropionate 17-isobutyrate, yield=75 mg.; λ$_{max}^{methanol}$ 235 sh (ε=11,000), 250 (ε=11,900) and 296 nm (ε=7,400).

B. Treat 9α-fluoro-16α-methyl-1,4-pregnadiene-11β,17α,21-triol-3,6,20-trione 17-propionate in a manner similar to that described in Example 10A. Isolate and purify the resultant product in a manner similar to that described to obtain. 9α-fluoro-16α-methyl-1,4,6-pregnatriene-6,11β,17α,21-tetrol-3,20-dione 6,17α,21-tripropionate; m.p. 114°-118° C.; $[\alpha]_D^{26}$ −49° (dioxane) λ$_{max}^{methanol}$ 224 (ε=12,100), 250 (ε=10,200) and 296 nm (ε=10,800).

C. Treat each of the following 6-keto-1,4-pregnadienes in a manner similar to that described in Example 10A but utilizing acetic anhydride instead of propionic anhydride:

9α-fluoro-16β-methyl-1,4-pregnadiene-11β,17α,21-triol-3,6,20-trione 17-propionate;

9α-fluoro-16β-methyl-1,4-pregnadiene-11β,17α,21-triol-3,6,20-trione 17-isobutyrate;

9α-fluoro-16β-methyl-1,4-pregnadiene-11β,17α,21-triol-3,6,20-trione 17-benzoate; and 9α-fluoro-16α-methyl-1,4-pregnadiene-11β,17α,21-triol-3,6,20-trione 17-valerate.

Isolate and purify each of the resultant products in a manner similar to that described in Example 10A to obtain, respectively, 9α-fluoro-16β-methyl-1,4,6-pregnatriene-6,11β,17α,21-tetrol-3,20-dione 6,21-diacetate 17-propionate; m.p. 133°–135° C.; $[\alpha]_D^{26}$ −15° (chloroform); $\lambda_{max}^{methanol}$ 225 ($\epsilon=10,600$), 250 ($\epsilon=9,800$) and 297 nm ($\epsilon=9,100$);

9α-fluoro-16β-methyl-1,4,6-pregnatriene-6,11β,17α,21-tetrol-3,20-dione 6,21-diacetate 17-isobutyrate; m.p. 135°–137° C.; $[\alpha]_D^{26}$ −16° (chloroform); $\lambda_{max}^{methanol}$ 224 ($\epsilon=11,700$), 250 ($\epsilon=10,100$) and 296 nm ($\epsilon=10,900$);

9α-fluoro-16β-methyl-1,4,6-pregnatriene-6,11β,17α,21-tetrol-3,20-dione 6,21-diacetate 17-benzoate; m.p. 175°–180° C.; and 9α-fluoro-16α-methyl-1,4,6-pregnatriene-6,11β,17α,21-tetrol-3,20-dione 6,21-diacetate 17-valerate; m.p. 105°–110° C.; $[\alpha]_D^{26}$ −51° (dioxane); $\lambda_{max}^{methanol}$ 224 ($\epsilon=10,800$), 257 ($\epsilon=9,600$) and 296 nm ($\epsilon=10,000$).

EXAMPLE 11

6-ETHOXYCARBONYLOXY-1,4,6-PREGNATRIENES

A.

9α-Fluoro-16β-Methyl-1,4,6-Pregnatriene-6,11β,17α,21-Tetrol-3,20-Dione 6-Ethylcarbonate 17,21-Dipropionate To a solution of 9α-fluoro-16β-methyl-1,4-pregnadiene-11β,17α,21-triol-3,6,20-trione 17,21-dipropionate (260 mg.) in 2,4,6-collidine (3 ml.) cooled to 5° C., add ethyl chloroformate (1 ml.), heat at 50° C. for 1 week, cool the reaction mixture and pour into dilute hydrochloric acid. Filter and wash the resultant precipitate, then purify the precipitate by chromatography on silica gel via gradient elution with ether containing increasing quantities of petroleum ether. Combine the like eluates containing the desired product as determined by thin layer chromatography, evaporate the combined eluates and crystallize the resultant residue from ether/isopropyl ether to obtain 9α-fluoro-16β-methyl-1,4,6-pregnatriene-6,11β,17α,21-tetrol-3,20-dione 6-ethylcarbonate 17,21-dipropionate, yield=124 mg.; m.p. 112°–116° C.; $[\alpha]_D^{26}$ −23° (chloroform); $\lambda_{max}^{methanol}$ 223 ($\epsilon=10,600$), 249 ($\epsilon=11,600$) and 293 nm ($\epsilon=8,400$).

B. In similar manner treat each of the 6-keto-1,4-pregnadiene starting compounds of Example 9B with ethyl chloroformate and isolate and purify each of the resultant products to obtain, respectively, 9α-fluoro-16β-methyl-1,4,6-pregnatriene-6,11β,17α,21-tetrol-3,20-dione 6-ethylcarbonate 21-acetate;

9α-chloro-16β-methyl-1,4,6-pregnatriene-6,11β,17α,21-tetrol-3,20-dione 6-ethylcarbonate 17,21-dipropionate;

9α-fluoro-16α,17α-isopropylidenedioxy-1,4,6-pregnatriene-6,11β,21-triol-3,20-dione 6-ethylcarbonate 21-acetate;

9α-fluoro-16α-methyl-1,4,6-pregnatriene-6,11β,17α,21-tetrol-3,20-dione 6-ethylcarbonate 21-acetate.

EXAMPLE 12

6-THIOETHOXYCARBONYLOXY-1,4,6-PREGNATRIENES

A.

9α-Fluoro-16β-Methyl-1,4,6-Pregnatriene-6,11β,17α,21-Tetrol-3,20-Dione 6-Thioethylcarbonate 21-Acetate To a solution of 9α-fluoro-16β-methyl-1,4-pregnadiene-11β,17α,21-triol-3,6,20-trione 21-acetate (200 mg.) in pyridine (2 ml.) cooled to 5° C., add ethyl chlorothiolformate (1 ml.). Allow the reaction mixture to stand at room temperature for 24 hours, then pour into dilute hydrochloric acid. Extract the aqueous mixture with methylene chloride, wash the combined methylene chloride extracts with water, then evaporate the extracts in vacuo. Chromatograph the resultant residue over silica gel via gradient elution with petroleum ether containing increasing quantities of ether. Combine the like fractions containing the desired product as determined by thin layer chromatography and evaporate the combined eluates and crystallize the resultant residue from methylene chloride/ether to give 9α-fluoro-16β-methyl-1,4,6-pregnatriene-6,11β,17α,21-tetrol-3,20-dione 6-thioethylcarbonate 21-acetate, yield=105 mg.; m.p. 175°–177° C., $[\alpha]_D^{26}$ +19° (chloroform); $\lambda_{max}^{methanol}$ 220 sh ($\epsilon=14,300$), 249 ($\epsilon=10,500$) and 296 nm ($\epsilon=10,600$).

B. Treat 9α-fluoro-16β-methyl-1,4-pregnadiene-11β,17α,21-triol-3,6,20-trione 17,21-dipropionate with ethyl chlorothiolformate in a manner similar to that described in Example 12A to obtain 9α-fluoro-16β-methyl-1,4,6-pregnatriene-6,11β,17α,21-tetrol-3,20-dione 6-thioethylcarbonate 17,21-dipropionate; m.p. 120°–125° C.; $[\alpha]_D^{26}$ −19° (chloroform); $\lambda_{max}^{methanol}$ 220 ($\epsilon=14,000$), 250 ($\epsilon=10,300$) and 294 nm ($\epsilon=10,700$).

EXAMPLE 13

6-THIOETHOXYTHIOCARBONYLOXY-1,4,6-PREGNATRIENES

A.

9α-Fluoro-16β-Methyl-1,4,6-Pregnatriene-6,11β,17α,21-Tetrol-3,20-Dione 6-Ethyl Dithiocarbonate 21-Acetate In the procedure of Example 12A by using an equivalent quantity of ethyl chlorodithioformate in place of ethyl chlorothiolformate, there is obtained the corresponding 6-ethyl dithiocarbonate derivative, i.e. 9α-fluoro-16β-methyl-1,4,6-pregnatriene-6,11β,17α,21-tetrol-3,20-dione 6-ethyl dithiocarbonate 21-acetate.

B. In similar manner, treat the last three 6-keto-1,4-pregnadiene starting compounds of Example 9B with ethyl chlorodithioformate in pyridine and isolate and purify each of the resultant products to obtain the corresponding 6-ethyl dithiocarbonate-1,4,6-pregnatriene derivative, respectively.

EXAMPLE 14

6-ACYLOXY-1,4,6-PREGNATRIENE-17α,21-DIOL-3,11,20-TRIONES

A.
9α-Fluoro-16β-Methyl-1,4,6-Pregnatriene-6,17α,21-Triol-3,11,20-Trione 6,21-Diacetate In a manner similar to that described in Example 9A treat 9α-fluoro-16β-methyl-1,4-pregnadiene-17α,21-diol-3,6,11,20-tetrone 21-acetate with acetic anhydride in pyridine. Isolate and purify the resultant product in a manner similar to that described to obtain 9α-fluoro-16β-methyl-1,4,6-pregnatriene-6,17α,21-triol-3,11,20-trione 6,21-diacetate.

B. Treat each of the 6,11-dioxo-1,4-pregnadienes prepared in Example 8B with acetic anhydride in pyridine in a manner similar to that described in Example 9A to obtain the corresponding 6-acyloxy-1,4,6-pregnatrienes, respectively, i.e.

9α-fluoro-16α-methyl-1,4,6-pregnatriene-6,17α,21-triol-3,11,20-trione 6,21-diacetate;
9α-chloro-16β-methyl-1,4,6-pregnatriene-6,17α,21-triol-3,11,20-trione 6-acetate 17,21-dipropionate;
9α-fluoro-16β-methyl-1,4,6-pregnatriene-6,17α,21-triol-3,11,20-trione 6acetate 17,21-dipropionate;
9α-fluoro-16α,17α-isopropylidenedioxy-1,4,6-pregnatriene-6,21-diol-3,11,20-trione 6,21-diacetate;
9α-fluoro-16β-methyl-1,4,6-pregnatriene-6,17α,21-triol-3,11,20-trione 6-acetate 21-trimethylacetate;
9α-fluoro-16α-methyl-1,4,6-pregnatriene-6,17α, 21-triol-3,11,20-trione 6acetate 21-trimethylacetate.

C. In the procedures of Examples 14A and 14B, by substituting for acetic anhydride equivalent quantities of the anhydride or acid chloride of other hydrocarbon-carboxylic acids, e.g. propionic anhydride or benzoyl chloride, there is obtained the corresponding 6-acyloxy derivative, e.g. the corresponding 6-propionate or 6-benzoate of the 6acetate products named therein, respectively.

Similarly, in the procedures of above Examples 14A and 14B, by substituting for acetic anhydride quivalent quantities of ethyl chloroformate or ethyl chlorothioformate or ethyl chlorodithioformate, there is obtained the corresponding 6-acyloxy derivative, i.e. the corresponding 6-ethyl carbonate or 6-ethyl thiocarbonate or 6-ethyl dithiocarbonate corresponding to the 6-acetate products named therein.

EXAMPLE 15

6-ACYLOXY-9-UNSUBSTITUTED-1,4,6-PREGNATRIENE-3,20-DIONES

A.
6β-Hydroxy-9-Unsubstituted-1,4-Pregnadiene-3,20-Diones

In a manner similar to that described in Preparation 1A, treat each of the following 9-unsubstituted-1,4-pregnadiene-3,20-diones in dry pyridine with benzoyl chloride under an atmosphere of nitrogen followed by isolation of the resulting 1,3,5-pregnatriene 3-benzoate and thence reaction thereof with oxygen in chloroform.

(1) 16α-methyl-21-chloro-1,4-pregnadiene-11β,17α-diol-3,20-dione 17-propionate,
(2) 16α-methyl-21-bromo-1,4-pregnadiene-11β,17α-diol-3,20-dione 17-propionate,
(3) 16α-methyl-21-fluoro-1,4-pregnadiene-11β,17α-diol-3,20-dione 17-propionate,
(4) 16α,17α-isopropylidenedioxy-1,4-pregnadiene-11β,21-diol-3,20-dione 21-propionate,
(5) 14α,17α-butylidenedioxy-1,4-pregnadiene-11β,21-diol-3,20-dione 21-propionate,
(6) 2′,2′-dimethyl-1,4-pregnadieno[17,16α-d]1′,3′-oxathiolane-21-ol-3,11,20-trione 21-propionate,
(7) D-homo 1,4-pregnadiene-11β,17α,21-triol-3,20-dione 17,21-dipropionate,
(8) n-butyl 3,20-dioxo-11β-hydroxy-16α-methyl-1,4-pregnadien-21-oate,
(9) propyl 2-chloro-3,20-dioxo-11β-hydroxy-16α-methyl-1,4-pregnadien-21-oate,
(10) 16β-methyl-20-chloromethoxy-21-nor-1,4-pregnadiene-11β,17α-diol-3,20-dione 17-propionate,
(11) 16β-methyl-20-fluoromethoxy-21-nor-1,4-pregnadiene-11β,17α-diol-3,20-dione 17-pripionate,
(12) 16-methylene-20-chloromethoxy-21-nor-1,4-pregnadiene-11β,17α-diol-3,20-dione 17-propionate,
(13) 16-fluoromethylene-1,4-pregnadiene-11β,17α,21-triol-3,20-dione 17,21-dipropionate,
(14) 16-chloromethylene-1,4-pregnadiene-17α,21-diol-3,11,20-trione 17-benzoate 21-propionate,
(15) 16-ethylidene-1,4-pregnadiene-17α,21-diol-3,11,20-trione 17,21-dipropionate,
(16) 16α,17α-cyclopentylidenedioxy-1,4-pregnadiene-11β,21-diol-3,20-dione 21-acetate,
(17) 16α-methyl-1,4-pregnadiene-11β,21-diol-3,20-dione 21-pivalate,
(18) 16β-methyl-21-nor-1,4-pregnadiene-11β,17α-diol-3,20-dione 20-methoxy 17-propionate,
(19) 14α,17α-(2′-butenylidenedioxy)-1,4-pregnadiene-11β,21-diol-3,20-dione 21-isonicotinate,
(20) 11β,21-dihydroxy-2′-methyl-5′β-H-1,4-pregnadieno[17,16α-d]-oxazoline-3,20-dione 21-acetate, Isolate and purify each of the resultant products in a manner similar to that described in Preparations 1–4 to obtain, respectively, the 6β-hydroxy derivative of each of the foregoing starting compounds.

B. 6-Oxo-9-Unsubstituted-1,4-Pregnadiene-3,20-Diones

In a manner similar to that described in Example 1A, treat each of the 6β-hydroxy-1,4-pregnadiene-3,20-diones prepared in Example 15A in benzene with N,N-dicyclohexylcarbodiimide and dimethylsulfoxide in the presence of trifluoroacetic acid and pyridine. Isolate and purify each of the resultant products in a manner similar to that described to obtain, respectively, the corresponding 6-oxo-9-unsubstituted-1,4-pregnadiene-3,20-diones.

C.
6-Acyloxy-9-Unsubstituted-1,4,6-Pregnatriene-3,20-Diones

In a manner similar to that described in Example 9A, treat each of the 6-oxo-9-unsubstituted-1,4-pregnadiene-3,20-diones prepared in Example 15B with acetic anhydride in pyridine at room temperature. Isolate and purify each of the resultant products in a manner similar to that described to obtain, respectively, (1) 16α-methyl-21-chloro-1,4,6-pregnatriene-6,11β,17α-triol-3,20-dione 6-acetate 17-propionate,
(2) 16α-methyl-21-bromo-1,4,6-pregnatriene-6,11β,17α-triol-3,20-dione 6-acetate 17-propionate,
(3) 16α-methyl-21-fluoro-1,4,6-pregnatriene-6,11β,17α-triol-3,20-dione 6-acetate 17-propionate,
(4) 16α,17α-isopropylidenedioxy-1,4,6-pregnatriene-6,11β,21-triol-3,20-dione 6-acetate 21-propionate, (5) 14α,17α-butylidenedioxy-1,4,6-pregnatriene-6,11β,21-triol-3,20-dione 6-acetate 21-propionate,
(6) 2',2'-dimethyl-1,4,6-pregnatrieno[17,16α-d]1',3'-oxathiolane-6,21-diol-3,11,20-trione 6acetate 21-propionate,
(7) D-homo 1,4,6-pregnatriene-6,11β,17α,21-tetrol-3,20-dione 6acetate 17,21-dipropionate,
(8) n-butyl 3,20-dioxo-6,11β-dihydroxy-16α-methyl-1,4,6-pregnatrien-21-oate 6acetate,
(9) propyl 2-chloro-3,20-dioxo-6,11β-dihydroxy-16α-methyl-1,4,6-pregnatrien-21-oate 6acetate,
(10) 16β-methyl-20-chloromethoxy-21-nor-1,4,6-pregnatriene-6,11β,17α-triol-3,20-dione 6-acetate 17-propionate,
(11) 16β-methyl-20-fluoromethoxy-21-nor-1,4,6-pregnatriene-6,11β,17α-triol-3,20-dione 6-acetate 17-propionate,
(12) 16-methylene-20-chloromethoxy-21-nor-1,4,6-pregnatriene-6,11β,17α-triol-3,20-dione 6-acetate 17-propionate,
(13) 16-fluoromethylene-1,4,6-pregnatriene-6,11β,17α,21-tetrol-3,20-dione 6-acetate 17,21-dipropionate,
(14) 16-chloromethylene-1,4,6-pregnatriene-6,17α,21-triol-3,11,20-trione 6-acetate 17-benzoate 21-propionate,
(15) 16-ethylidene-1,4,6-pregnatriene-6,17α,21-triol-3,11,20-trione 6-acetate 17,21-dipropionate,
(16) 16α,17α-cyclopentylidenedioxy-1,4,6-pregnatriene-6,11β,21-triol-3,20-dione 6,21-diacetate,
(17) 16α-methyl-1,4,6-pregnatriene-6,11β,21-triol-3,20-dione 6-acetate 21-pivalate,
(18) 16β-methyl-21-nor-1,4,6-pregnatriene-6,11β,17α-triol-3,20-dione-20-methoxy 6-acetate 17-propionate,
(19) 14α,17α-(2'-butenylidenedioxy)-1,4,6-pregnatriene-6,11β,21-triol-3,20-dione 6acetate 21-isonicotinate,
(20) 6,11β,21-trihydroxy-2'-methyl-5'βH-1,4,6-pregnatrieno[17,16α-d]-oxazoline-3,20-dione 6,21-diacetate,

EXAMPLE 16

6-ACYLOXY-9-HALOGENO-1,4,6-PREGNATRIENE-3,20-DIONES

A.
6β-Hydroxy-9-Halogeno-1,4-Pregnadiene-3,20-Diones

In a manner similar to that described in Preparation 1A, treat each of the following 9-halogeno-1,4-pregnadiene-3,20-diones in dry pyridine with benzoyl chloride under an atmosphere of nitrogen followed by isolation of the resulting 1,3,5-pregnatriene 3-benzoate and thence reaction thereof with oxygen in chloroform.
(1) 9α-fluoro-11β,21-dihydroxy-2'-methyl-5'βH-1,4-pregnadieno-[17,16α-d]oxazoline-3,20-dione 21-acetate,
(2) 9α-fluoro-16α,17α-cyclohexylidenedioxy-1,4-pregnadiene-11β,21-diol-3,20-dione 21-acetate,
(3) 9α-fluoro-11β,21-dihydroxy-2',2'-dimethyl-1,4-pregnadieno-[17,16α-d]1',3'-oxathiolane-3,20-dione 21-propionate,
(4) 9α-chloro-11β,21-dihydroxy-2',2'-dimethyl-1,4-pregnadieno-[17,16α-d]1',3'-oxathiolane-3,20-dione 21-propionate,
(5) 9α-fluoro-16β-methyl-20-fluoromethoxy-21-nor-1,4-pregnadiene-11β,17α-diol-3,20-dione 17-propionate,
(6) 9α-fluoro-16β-methyl-20-chloromethoxy-21-nor-1,4-pregnadiene-11β,17α-diol-3,20-dione 17-propionate,
(7) 9α-chloro-16α-methyl-1,4-pregnadiene-11β,21-diol-3,20-dione 21-acetate,
(8) 9α-fluoro-16-methylene-20-fluoromethoxy-21-nor-1,4-pregnadiene-11β,17α-diol-3,20-dione 17-propionate,
(9) 9α-fluoro-16-methylene-20-chloromethoxy-21-nor-1,4-pregnadiene-11β,17α-diol-3,20-dione 17-propionate,
(10) 9α-fluoro-16-fluoromethylene-1,4-pregnadiene-11β,17α,21-triol-3,20-dione 21-propionate,
(11) n-butyl 9α-fluoro-11β-hydroxy-16α,17α-isopropylidenedioxy-3,20-dioxo-1,4-pregnadien-21-oate,
(12) 9α-chloro-11β-fluoro-16β-methyl-1,4-pregnadiene-17α,21-diol-3,20-dione 21-propionate,
(13) 9α-bromo-11β-chloro-1,4-pregnadiene-17α,21-diol-3,20-dione 21-acetate,
(14) n-butyl 9α-chloro-11β-fluoro-14α,17α-ethylidenedioxy-3,20-dioxo-1,4-pregnadien-21-oate.

Isolate and purify each of the resulting products in a manner similar to that described in Preparations 1–4 to obtain the corresponding 6β-hydroxy derivative of each of the foregoing starting compounds.

B. 6-Oxo-9α-Halogeno-1,4-Pregnadiene-3,20-Diones

In a manner similar to that described in Example 1A, treat each of the 6β-hydroxy-9-halogeno-1,4-pregnadiene-3,20-diones prepared in Example 16A in benzene with N,N-dicyclohexylcarbodiimide and dimethylsulfoxide in the presence of trifluoroacetic acid and pyridine. Isolate and purify each of the resultant products in a manner similar to that described to obtain the 6-oxo derivative corresponding to each of the 6β-hydroxy starting compounds.

C.
6-Acyloxy-9-Halogeno-1,4,6-Pregnatriene-3,20-Diones

In a manner similar to that described in Example 9, treat each of the 6β-oxo-9α-halogeno-1,4-pregnadiene-3,20-diones of Example 16B with acetic anhydride in pyridine. Isolate and purify each of the resultant products in a manner similar to that described to obtain, respectively,
(1) 9α-fluoro-6,11β,21-trihydroxy-2'-methyl-5'βH-1,4,6-pregnatrieno[17,16α-d]oxazoline-3,20-dione 6,21-diacetate,
(2) 9α-fluoro-16α,17α-cyclohexylidenedioxy-1,4,6-pregnatriene-6,11β,21-triol-3,20-dione 6,21-diacetate,
(3) 9α-fluoro-6,11β,21-trihydroxy-2',2'-dimethyl-1,4,6-pregnatrieno[17,16α-d]1'3'-oxathiolane-3,20-dione 6-acetate 21-propionate,
(4) 9α-chloro-6,11β,21-trihydroxy-2',2'-dimethyl-1,4,6-pregnatrieno[17,16α-d]1',3'-oxathiolane-3,20-dione 6-acetate 21-propionate,
(5) 9α-fluoro-16β-methyl-20-fluoromethoxy-21-nor-1,4,6-pregnatriene-6,11β,17α-triol-3,20-dione 6-acetate 17-propionate,
(6) 9α-fluoro-16β-methyl-20-chloromethoxy-21-nor-1,4,6-pregnatriene-6,11β,17α-triol-3,20-dione 6-acetate 17-propionate,
(7) 9α-chloro-16α-methyl-1,4,6-pregnatriene-6,11β,21-triol-3,20-dione 6,21-diacetate, (8) 9α-fluoro-16-methylene-20-fluoromethoxy-21-nor-1,4,6-pregnatriene-6,11β,17α-triol-3,20-dione 6-acetate 17-propionate, (9) 9α-fluoro-16-methylene-20-chloromethoxy-21-nor-1,4,6-pregnatriene-6,11β,17α-triol-3,20-dione 6-acetate 17-propionate,

(10) 9α-fluoro-16-fluoromethylene-1,4,6-pregnatriene-6,11β,17α,21-tetrol-3,20-dione 6-acetate 21-propionate,

(11) n-butyl 9α-fluoro-6,11β-dihydroxy-16α,17α-isopropylidenedioxy-3,20-dioxo-1,4,6-pregnatrien-21-oate 6-acetate,

(12) 9α-chloro-11β-fluoro-16β-methyl-1,4,6-pregnatriene-6,17α,21-triol-3,20-dione 6-acetate 21-propionate,

(13) 9α-bromo-11β-chloro-1,4,6-pregnatriene-6,17α,21-triol-3,20-dione 6,21-diacetate,

(14) n-butyl 6-hydroxy-9α-chloro-11β-fluoro-14α,17α-ethylidenedioxy-3,20-dioxo-1,4,6-pregnatrien-21-oate 6-acetate.

EXAMPLE 17

9α-FLUORO-16β-METHYL-1,4,6-PREGNATRIENE-6,11β,17α-TRIOL-3,20,21-TRIONE 6-ACETATE 17-PROPIONATE AND THE 21-DIMETHYL KETAL THEREOF

A.

9α-Fluoro-16β-Methyl-1,4-Pregnadiene-11β,17α,21-Triol-3,6,20-Trione 17α,21-Ethylorthopropionate To a solution of 9α-fluoro-16β-methyl-1,4-pregnadiene-11β,17α,21-triol-3,6,20-trione (0.5 gms.) in dimethylsulfoxide (7 ml.), add triethylorthopropionate (0.7 ml.) and p-toluenesulfonic acid (70 mg.). Stir the reaction mixture at room temperature for 5 hours, then pour into dilute aqueous sodium bicarbonate and extract with ethyl acetate. Wash the combined extracts with water, dry over magnesium sulfate, evaporate, and crystallize the resultant residue from ether to obtain 9α-fluoro-16β-methyl-1,4-pregnadiene-11β,17α,21-triol-3,6,20-trione 17α,21-ethylorthopropionate.

B.

9α-Fluoro-16β-Methyl-1,4,6-Pregnatriene-6,11β,17α,21-Tetrol-3,20-Dione 17α,21-Ethylorthopropionate 6-Acetate To a solution of 9α-fluoro-16β-methyl-1,4-pregnadiene-11β,17α,21-triol-3,6,20-trione 17α,21-ethylorthopropionate (350 mg.) in pyridine (3 ml.), add acetic anhydride (1 ml.). Allow the reaction mixture to stand at room temperature for 5 hours, then pour into water and extract with ethyl acetate. Wash the combined ethyl acetate extracts with water, dry over magnesium sulfate, evaporate in vacuo, and purify the resultant residue by chromatography on silica gel using gradient elution with ether/petroleum ether. Combine the like eluates containing the desired product as determined by thin layer chromatography and evaporate to a residue comprising 9α-fluoro-16β-methyl-1,4,6-pregnatriene-6,11β,17α,21-tetrol-3,20-dione 6-acetate 17α,21-ethylorthopropionate.

C.

9α-Fluoro-16β-Methyl-1,4,6-Pregnatriene-6,11β,17α,21-Tetrol-3,20-Dione 6-Acetate 17-Propionate Prepare a solution of 9α-fluoro-16β-methyl-1,4,6-pregnatriene-6,11β,17α,21-tetrol-3,20-dione 6-acetate 17α,21-ethylorthopropionate (0.5 gms.) in acetic acid/water (9:1, 10 ml.), and stir at room temperature overnight. Pour the reaction mixture into ethyl acetate, wash with water followed by aqueous sodium bicarbonate, and then again with water. Evaporate the ethyl acetate solution in vacuo and crystallize the resultant residue from ether to obtain 9α-fluoro-16β-methyl-1,4,6-pregnatriene-6,11β,17α,21-tetrol-3,20-dione 6-acetate 17-propionate.

D.

9α-Fluoro-16β-Methyl-1,4,6-Pregnatriene-6,11β,17α-Triol-3,20,21-Trione 6-Acetate 17-Propionate To a solution of 9α-fluoro-16β-methyl-1,4,6-pregnatriene-6,11β,17α,21-tetrol-3,20-dione 6-acetate 17-propionate (250 mg.) in methanol (25 ml.) containing cupric acetate (10 mg.) bubble oxygen for 19 hours at room temperature with stirring, then add a solution of ethylenediaminetetraacetic acid disodium salt (25 mg.) in water (1.5 ml.) and evaporate the solvents in vacuo. Dissolve the resultant residue in ethyl acetate (30 ml.), then wash the ethyl acetate solution with water and dry over magnesium sulfate. Evaporate the solvent in vacuo and crystallize the resultant residue from ether to obtain 9α-fluoro-16β-methyl-1,4,6-pregnatriene-6,11β,17α-triol-3,20,21-trione 6-acetate 17-propionate.

E.

9α-Fluoro-16β-Methyl-1,4,6-Pregnatriene-6,11β,17α-Triol-3,20,21-Trione 6-Acetate 17-Propionate 21-Dimethyl Ketal Prepare a solution of 9α-fluoro-16β-methyl-1,4,6-pregnatriene-6,11β,17α-triol-3,20,21-trione 6-acetate 17-propionate (200 mg.) in dry methanol (20 ml.) and anhydrous p-toluenesulfonic acid (10 mg.). Allow the solution to stand at room temperature overnight, then pour into dilute aqueous sodium bicarbonate and extract with ether. Wash the combined ether extracts with water and dry over magnesium sulfate. Evaporate the solvent in vacuo and chromatograph the resultant residue over silica gel using petroleum ether/ether gradient elution. Combine the like fractions containing the desired product as determined by thin layer chromatography and evaporate, then crystallize the resultant residue from ether to obtain 9α-fluoro-16β-methyl-1,4,6-pregnatriene-6,11β,17α-triol-3,20,21-trione 6-acetate 17-propionate 21-dimethyl ketal.

EXAMPLE 18

9α-FLUORO-16β-METHYL-1,4,6-PREGNATRIENE-6,11β,17α,21-TETROL-3,20-DIONE 6-PROPIONATE

A.

9α-Fluoro-16β-Methyl-1,4-Pregnadiene-11β,17α,21-Triol-3,6,20-Trione 21-Methoxyethoxymethyl Ether Dissolve 9α-fluoro-16β-methyl-1,4-pregnadiene-11β,17α,21-triol-3,6,20-trione (812 mg.) in acetonitrile (30 ml.) containing methoxyethoxymethyl triethyl ammonium chloride (450 mg.). Stir the reaction mixture for 30 minutes, then pour into water, separate the resultant precipitate by filtration, wash with water, dry and crystallize from ether to obtain 9α-fluoro-16β-methyl-1,4-pregnadiene-11β,17α,21-triol-3,6,20-trione 21-methoxyethoxymethyl ether.

B.
9α-Fluoro-16β-Methyl-1,4,6-Pregnatriene-6,11β,17α,21-Tetrol-3,20-Dione 6-Propionate 21-Methoxyethoxymethyl Ether To a solution of 9α-fluoro-16β-methyl-1,4-pregnadiene-11β,17α,21-triol-3,6,20-trione 21-methoxyethoxymethyl ether (500 mg.) in pyridine (6 ml.) add propionic anhydride (2 ml.) and allow to stand at room temperature for 5 hours. Pour the reaction mixture into dilute hydrochloric acid, separate the resultant precipitate by filtration, wash with water, dry and re-crystallize from ether to obtain 9α-fluoro-16β-methyl-1,4,6-pregnatriene-6,11β,17α,21-tetrol-3,20-dione 6-propionate 21-methoxyethoxymethyl ether.

C.
9α-Fluoro-16β-Methyl-1,4,6-Pregnatriene-6,11β,17α,21-Tetrol-3,20-Dione 6-Propionate To a solution of 9α-fluoro-16β-methyl-1,4,6-pregnatriene-6,11β,17α,21-tetrol-3,20-dione 6-propionate 21-methoxyethoxymethyl ether (500 mg.) in methylene chloride (25 ml.) at room temperature add with rapid stirring finely powdered zinc bromide (1.22 gms., 5 equivalents). Monitor the course of the reaction by thin layer chromatography and, when the reaction is complete, wash the reaction mixture with aqueous sodium bicarbonate, then water, then dry the organic solution over magnesium sulfate and evaporate in vacuo and crystallize the resultant residue from ether to obtain 9α-fluoro-16β-methyl-1,4,6-pregnatriene-6,11β,17α,21-tetrol-3,20-dione 6-propionate.

EXAMPLE 19
9α-CHLORO-16β-METHYL-1,4-PREGNADIENE-6,11β,17α,21,21-PENTOL-3,20-DIONE 6,21,21-TRIACETATE

A.
9α-Chloro-16β-Methyl-1,4-Pregnadiene-11β,17α-Diol-3,6,20,21-Tetrone

The requisite intermediate, 9α-chloro-16β-methyl-1,4-pregnadiene-11β,17α,21-triol-3,6,20-trione, is prepared from 9α-chloro-16β-methyl-1,4-pregnadiene-11β,17α,21-triol-3,20-dione 21-acetate utilizing procedures similar to those described in Preparation 1 and Examples 1 and 5.

Into a solution of 9α-chloro-16β-methyl-1,4-pregnadiene-11β,17α,21-triol-3,6,20-trione (250 mg.) in methanol (25 ml.) containing cupric acetate (10 mg.) bubble oxygen for 19 hours at room temperature with stirring. To the reaction mixture add a solution of ethylenediaminetetraacetic acid disodium salt (25 mg.) in water (1.5 ml.), then evaporate the solvents in vacuo. Dissolve the resultant residue in ethyl acetate (30 ml.), wash the ethyl acetate solution with water, and dry over magnesium sulfate. Evaporate the solvent in vacuo and crystallize the resultant residue from ether to obtain 9α-chloro-16β-methyl-1,4-pregnadiene-11β,17α-diol-3,6,20,21-tetrone.

B.
9α-Chloro-16β-Methyl-1,4,6-Pregnatriene-6,11β,17α,21,21-Pentol-3,20-Dione 6,21,21-Triacetate To a solution of 9α-chloro-16β-methyl-1,4-pregnadiene-11β,17α-diol-3,6,20,20-tetrone (200 mg.) in pyridine (3 ml.), add acetic anhydride (1 ml.), and allow to stand at room temperature for 5 hours. Add water to the reaction mixture, extract with ether, wash the combined ether extracts with water, dry over magnesium sulfate and evaporate in vacuo. Chromatograph the resultant residue on silica gel using petroleum ether/ether gradient elution. Combine the like fractions containing the desired compound as determined by thin layer chromatography, and evaporate in vacuo to a residue comprising 9α-chloro-16β-methyl-1,4,6-pregnatriene-6,11β,17α,21,21-pentol-3,20-dione 6,21,21-triacetate.

I claim:

1. A 6-acyloxy-3,20-dioxo-1,4,6-pregnatriene of the following formula I:

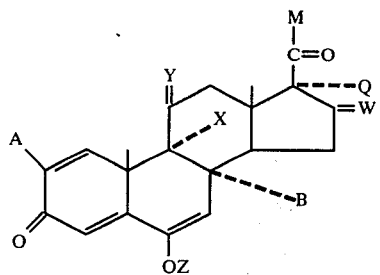

wherein

A is hydrogen or, provided Y is (H,βOH), A is chlorine, fluorine or methyl;

B is hydrogen or, together with Q, is a 14α,17α-alkylidenedioxy derivative;

X is hydrogen, fluorine or chlorine;

Y is oxygen, (H,βOH), (H,βOCOH); or (H,β-chlorine) or (H,β-fluorine) provided X is chlorine;

Z is hydrocarboncarbonyl, alkoxycarbonyl, thioalkoxycarbonyl, or thioalkoxythiocarbonyl wherein Z has up to 12 carbon atoms;

Q is hydrogen provided W is (H, lower alkyl); or OV wherein V is hydrogen or an acyl radical of a hydrocarboncarboxylic acid having up to 12 carbon atoms or an acyl radical of benzoic acid substituted by a halogen or methoxy group or an acyl radical of retinoic acid provided W is other than (H,α-retinoyloxy);

W is (H, lower alkyl); (H,α-OV$_1$) wherein V$_1$ is hydrogen or an acyl radical of an acid selected from the group consisting of a hydrocarboncarboxylic acid having up to 12 carbon atoms, benzoic acid substituted by a halogen or methoxy group, retinoic acid, and isonicotinic acid; =CHT wherein T is hydrogen, lower alkyl, fluorine or chlorine, and W and Q taken together is a 16α,17α-lower alkylidenedioxy; a 16α,17α-cycloalkylidenedioxy; the grouping

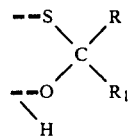

wherein R and R$_1$ are lower alkyl; or the grouping

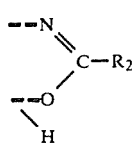

wherein R₂ is lower alkyl or phenyl;

M is —OR₃ when Q is O-acyl, R₃ being lower alkyl or halogeno lower alkyl; —CHO, acetals, hemiacetals and acylals thereof; —COOR₄ wherein R₄ is alkyl having up to 12 carbon atoms; —CH₂G wherein G is halogen having an atomic weight of less than 100 provided Q is not hydrogen, or G is OV₂ wherein V₂ is hydrogen, an acyl radical of an acid selected from the group consisting of a hydrocarboncarboxylic acid having up to 12 carbon atoms, benzoic acid substituted by a halogen or methoxy group, retinoic acid, isonicotinic acid, or phosphoric acid and mono- and dialkali and alkaline earth metal salts thereof; and G together with Q is an alkylidenedioxy or an alkylorthoalkanoate;

and the 1,2-dihydro analogs of the foregoing.

2. A compound of claim 1, formula I, wherein X is fluorine or chlorine and Y is (H,βOH).

3. A compound of claim 1, formula I, wherein M is CH₂OV₂; Q is OV; A, B are hydrogen; X is fluorine or chlorine; and Y is (H,62 OH).

4. A compound of claim 3 wherein X is fluorine and W is (H,CH₃), said compound having the following formula:

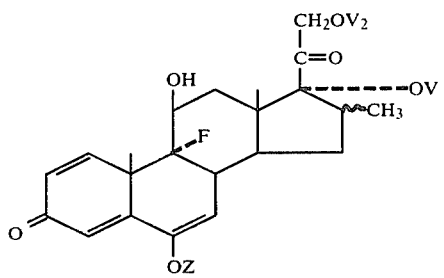

wherein V and V₂ are each hydrogen or an acyl radical of a hydrocarboncarboxylic acid having up to 12 carbon atoms.

5. A 16β-methyl-1,4,6-pregnatriene of claim 4 wherein V is an acyl radical of a hydrocarboncarboxylic acid having up to 8 carbon atoms.

6. A compound of claim 5 wherein each of V and V₂ is an acyl radical of a lower alkanoic acid having two to four carbon atoms and Z is a hydrocarboncarbonyl having up to eight carbon atoms.

7. A compound of claim 6 which is 9α-fluoro-16β-methyl-1,4,6-pregnatriene-6,11β,17α,21-tetrol-3,20-dione 6,17,21-tripropionate.

8. A compound of claim 6 which is 9α-fluoro-16β-methyl-1,4,6-pregnatriene-6,11β,17α,21-tetrol-3,20-dione 6,21-dipropionate 17-isobutyrate.

9. A compound of claim 3 which is 9α-chloro-16β-methyl-1,4,6-pregnatriene-6,11β,17α,21-tetrol-3,20-dione 6-acetate 17,21-dipropionate.

10. A compound of claim 2 which is 9α-fluoro-16α,17α-isopropylidenedioxy-1,4,6-pregnatriene-[6,21-diol] 6,11β,21-triol-3,20-dione 6,21-diacetate.

11. A compound of claim 4 which is 9α-fluoro-16α-methyl-1,4,6-pregnatriene-6,11β,17α,21-tetrol-3,20-dione 6,17,21-tripropionate.

12. The method of treating an inflammatory condition in a warm-blooded animal which comprises administering to said animal a non-toxic, anti-inflammatory effective amount of a 6-acyloxy-3,20-dioxo-1,4,6-pregnatriene of formula I, claim 1, or of a 1,2-dihydro analog thereof;

together with a non-toxic, pharmaceutically acceptable carrier.

13. The method of claim 12 which comprises topically administering to said animal a non-toxic, anti-inflammatory effective amount of a 6-acyloxy-16β-methyl-3,20-dioxo-1,4,6-pregnatriene of claim 5.

14. A pharmaceutical composition for use in the treatment of inflammation which comprises a 6-acyloxy-3,20-dioxo-1,4,6-pregnatriene of formula I, claim 1, or a 1,2-dihydro analog thereof;

together with a non-toxic, pharmaceutically acceptable carrier.

15. A 3,6,20-trioxo-1,4-pregnadiene of the following formula:

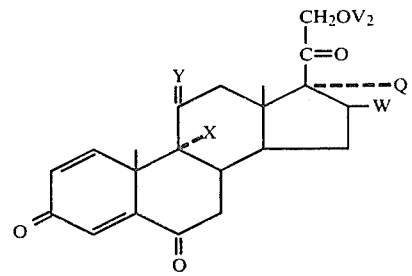

wherein

X is hydrogen, fluorine, or chlorine;

Y is (H,βOH), or (H,β-chlorine) provided X is chlorine;

Q is hydroxy or OV wherein V is an acyl radical of a hydrocarboncarboxylic acid having up to 8 carbon atoms;

V₂ is hydrogen or an acyl radical of a hydrocarboncarboxylic acid having up to 8 carbon atoms; and OV₂ together with Q is an alkylidenedioxy or an alkylorthoalkanoate;

W is (H,CH₃), methylene, (H,αOV₂) wherein V₂ is as hereinabove defined;

or together, W and Q form an alkylidenedioxy group or the grouping

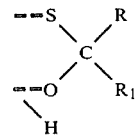

wherein R and R₁ are lower alkyl; or the grouping

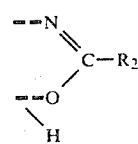

wherein R₂ is lower alkyl or phenyl.

16. A compound of claim 15 wherein X is fluorine, Y is (H,βOH), W is (H,CH₃); and Q is OV, said compound having the formula:

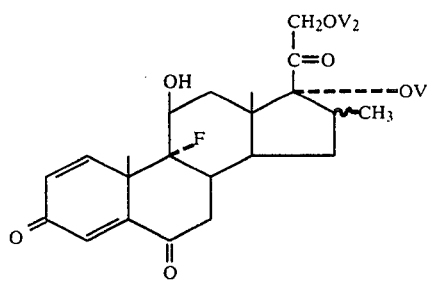

wherein V and V₂ are as defined in claim 15.

17. A compound of claim 16 wherein V is isobutyryl and V₂ is hydrogen.

18. A 16β-methyl compound of claim 16 wherein V is hydrocarboncarbonyl having up to 8 carbon atoms.

19. A compound of claim 18 which is 9α-fluoro-16β-methyl-1,4-pregnadiene-11β,17α,21-triol-3,6,20-trione 17,21-dipropionate.

20. A compound of claim 18 which is 9α-fluoro-16β-methyl-1,4-pregnadiene-11β,17α,21-triol-3,6,20-trione 17-valerate.

21. A compound of claim 15 which is 9α-fluoro-16α,17α-isopropylidenedioxy-1,4-pregnadiene-11β,21-diol-3,6,20-trione 21-acetate.

22. A pharmaceutical composition comprising a 3,6,20-trioxo-1,4-pregnadiene of claim 15 together with a non-toxic, pharmaceutically acceptable carrier.

23. The method of treating an inflammatory condition in a warm-blooded animal which comprises administering to said animal a non-toxic, anti-inflammatory active amount of a 3,6,20-trioxo-1,4-pregnadiene of claim 15, together with a non-toxic, pharmaceutically acceptable carrier.

24. The method of claim 23 which comprises topically administering to said animal a non-toxic, anti-inflammatory effective amount of a 3,6,20-trioxo-1,4-pregnadiene of claim 18.

25. The process for the preparation of a 3-oxo-6-acyloxy-1,4,6-pregnatriene of formula I, claim 1, or the 1,2-dihydro analog thereof wherein said acyl is an acid radical of an acid selected from the group consisting of a hydrocarboncarboxylic acid, an alkylcarbonic acid, an alkylthiocarbonic acid, and an alkyldithiocarbonic acid, said acid radical having up to 12 carbon atoms, which comprises the reaction of the corresponding 3,6-dioxo-6,7-dihydro-1,4-pregnadiene or 3,6-dioxo-6,7-dihydro-4-pregnene with an acid anhydride or an acid halide of said acid in a tertiary amine.

26. The process of claim 25 wherein said tertiary amine is pyridine.

27. The process of claim 25 wherein said tertiary amine is pyridine and wherein said 3,6-dioxo-1,4-pregnadiene reacts with an acid anhydride or an acid chloride of a lower alkanoic acid having up to 3 carbon atoms whereby is formed a 6-lower alkanoyloxy-1,4,6-pregnatriene.

28. The process of claim 25 wherein said tertiary amine is pyridine and wherein said 3,6-dioxo-1,4-pregnadiene reacts with an acid halide selected from the group consisting of benzoyl chloride, ethylchlorothiolformate, ethylchloroformate, whereby is formed a 6-benzoyloxy-1,4,6-pregnatriene, a 6-thioethoxycarbonyl-1,4,6-pregnatriene and a 6-ethoxycarbonyl-1,4,6-pregnatriene, respectively.

29. A compound of claim 3 which is 9α-fluoro-16β-methyl-1,4,6-pregnatriene-6,11β,17α,21-tetrol-3,20-dione 6-ethylcarbonate 17,21-dipropionate.

30. A compound of claim 3 which is 9α-fluoro-16β-methyl-1,4,6-pregnatriene-6,11β,17α,21-tetrol-3,20-dione 6-thioethyl-carbonate 21-acetate.

* * * * *

UNITED STATES PATENT AND TRADEMARK OFFICE
CERTIFICATE OF CORRECTION

PATENT NO. : 4,201,778
DATED : May 6, 1980
INVENTOR(S) : Richard W. Draper

It is certified that error appears in the above-identified patent and that said Letters Patent are hereby corrected as shown below:

Claim 1, Column 38, line 22, " 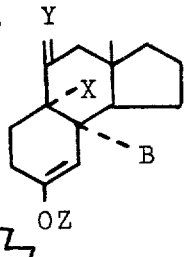 " should read

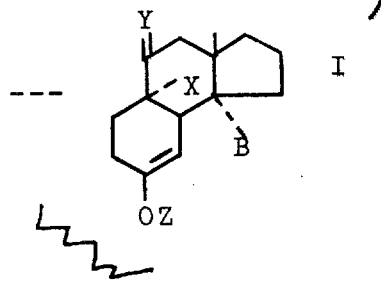

Claim 3, column 39, line 29, "Y is (H,62OH)." should read ---Y is (H,βOH

Claim 10, column 39, lines 67 & 68, "pregnatriene-/ 6,21-diol_/-6,11β,21-triol-" should read ---pregnatriene-6,11β,21-triol---.

Signed and Sealed this

Fifth Day of August 1980

[SEAL]

Attest:

SIDNEY A. DIAMOND

Attesting Officer    Commissioner of Patents and Trademarks